United States Patent
Ren et al.

(10) Patent No.: US 9,370,189 B2
(45) Date of Patent: Jun. 21, 2016

(54) CONTROLLING PSEUDOMONAS AERUGINOSA PERSISTER CELLS WITH GM-CSF

(71) Applicants: Dacheng Ren, Syracuse, NY (US); Geetika S Choudhary, Syracuse, NY (US); Xiangyu Yao, Liverpool, NY (US)

(72) Inventors: Dacheng Ren, Syracuse, NY (US); Geetika S Choudhary, Syracuse, NY (US); Xiangyu Yao, Liverpool, NY (US)

(73) Assignee: Syracuse University, Syracuse, NY (US)

( * ) Notice: Subject to any disclaimer, the term of this patent is extended or adjusted under 35 U.S.C. 154(b) by 126 days.

(21) Appl. No.: 13/897,842

(22) Filed: May 20, 2013

(65) Prior Publication Data
US 2014/0010778 A1   Jan. 9, 2014

Related U.S. Application Data

(60) Provisional application No. 61/648,671, filed on May 18, 2012.

(51) Int. Cl.
| | |
|---|---|
| A61K 38/19 | (2006.01) |
| A01N 63/02 | (2006.01) |
| C12Q 1/18 | (2006.01) |
| A61K 38/51 | (2006.01) |
| A61K 31/65 | (2006.01) |
| A61K 31/7036 | (2006.01) |
| A61K 31/496 | (2006.01) |

(52) U.S. Cl.
CPC .............. *A01N 63/02* (2013.01); *A61K 31/496* (2013.01); *A61K 31/65* (2013.01); *A61K 31/7036* (2013.01); *A61K 38/193* (2013.01); *A61K 38/51* (2013.01); *C12Q 1/18* (2013.01); *C12Y 402/02003* (2013.01); *G01N 2333/52* (2013.01); *G01N 2333/535* (2013.01)

(58) Field of Classification Search
CPC .................................................. A61K 38/193
See application file for complete search history.

(56) References Cited

U.S. PATENT DOCUMENTS

2009/0074712 A1* 3/2009 Frith ............................ 424/85.2
2012/0053155 A1   3/2012 Ren et al.

FOREIGN PATENT DOCUMENTS

| WO | 2008/052567 | 5/2008 |
| WO | 2011/019736 | 2/2011 |

OTHER PUBLICATIONS

Lee et al. Modulation of Bacterial Growth by Tumor Necrosis Factor-alpha In Vitro and In Vivo. American Journal Respiratory and Critical Care Medicine. 2003; 168: 1462-1470.*
McLaughlin et al. Interleukin-1 beta-induced growth enhancement of *Staphylococcus aureus* occurs in biofilm but not planktonic cultures. Microbial Pathogenesis. 2006 41:67-79.*
Cotton et al. The Role of Alginate in P. aeruginosa PAO1 Biofilm Structural Resistance to Gentamicin and Ciprofloxacin. Journal of Experimental Microbiology and Immunology. 2009; 13:58-62.*
Hubei et al. The Journal of Infectious Diseases 2002;185:1490-501.*
Tanaka et al, Infection and Immunity, 1989, vol. 57, No. 6, pp. 1792-1799.*
Mayer et al , The Journal of Infectious Diseases, vol. 163:584-590.*
Jensen, P.O. et al., 'Increased serum concentration of G-CSF in cystic fibrosis patients with chronic Pseudomonas aeruginosa pneumonia', Journal of Cystic Fibrosis, Feb. 28, 2006, vol. 5, Np. 3, pp. 145-151, ISSN 1569-1993.
Rybkte, Morten, et al., 'The implicaton of Pseudomonas aeruginosa biofilms in infections', Inflammation & Allergy-Drug Targets, vol. 10, No. 2, Apr. 1, 2011, pp. 141-157, ISSN 1871-5281, see abstract; p. 148, left column.
Chen, XI., et al., 'Control of bacterial persister cells by Trp/Arg-containing antimicrobial peptides', Applied and environmental microbiology, May 27, 2011, vol. 77, No. 14, pp. 4878-4885, ISSN 0099-2240, see abstract; materials and methods.
International Search Report Form PCT/ISA/210, International Application No. PCT/US2013/041821, pp. 1-10, Dated Jul. 29, 2013.
Heslet, L., Bay, C., Nepper-Christensen, S.; The Immunomodulatory Effect of Inhaled Granuloctye-macrophage Colony-Stimulating Factor in Cystic Fibrosis. A New Tratment Paradigm; Journal of Inflammation Research; 2012; vol. 5; pp. 19-27.
Lamppa, J., Ackerman, M., Lai, J., Scanlon, T., Griswold, K., Genetically Engineered Alginate Lyase-PEG conjugates Exhibit Enhanced Catalytic Function and Reduced Immunoreactivity; PLoS one; Feb. 2011; vol. 6; Issue 2.
Alkawash, M., Soothill, J., Schiller, N.; Alginate Lyase Enhances Antibiotic Killing of Mucoid Pseudomonas Aeruginosa in Biofilms; Journal Compilations; 2005; vol. 114; pp. 131-138.
Hatch, R., Schiller, N.; Alginate Lyase Promotes Diffusion of Aminoglycosides Through the Extracellular Polysaccharide of Mucoid Pseudomonas Aeruginosa; Antimicrobial Agents and Chemotherapy; Apr. 1998; vol. 42, No. 4; pp. 974-977.
Supplementary European Search Report of Application No. EP13791371 dated Oct. 9, 2015.

* cited by examiner

*Primary Examiner* — Prema Mertz
(74) *Attorney, Agent, or Firm* — Bond Schoeneck & King, PLLC; Frederick Price; George McGuire

(57) ABSTRACT

The present invention relates to host immune factors and antibiotics and, more particularly, to a system and method for controlling and reducing the antibiotic tolerance of bacterial persister cells with host immune factors.

3 Claims, 21 Drawing Sheets

CONTROLLING PSEUDOMONAS AERUGINOSA PERSISTER CELLS WITH GM-CSF

1. STATEMENT REGARDING FEDERALLY SPONSORED RESEARCH OR DEVELOPMENT

This invention was made with government support under Grant No. 1137186 which was awarded by the NSF-EFRI. The government has certain rights in the invention.

BACKGROUND OF THE INVENTION

1. Field of the Invention

The present invention relates to host immune factors and antibiotics and, more particularly, to a system and method for controlling and reducing the antibiotic tolerance of bacterial persister cells with host immune factors.

2. Description of the Related Art

Recent research has shown that persister cells play important roles in intrinsic antibiotic resistance of bacteria. Persister cells are a small subpopulation of dormant phenotypic variants, which can be found in many bacterial species. The dormant nature of persister cells allows this subpopulation to survive the attack of almost all classes of antibiotics. Thus, when an antibiotic therapy is stopped, the surviving persisters relapse to normal cells causing chronic infections with recurring symptoms. Persister formation increases in biofilms, which are complex communities of cells that grow on surfaces and protected by an extracellular polysaccharide matrix secreted by attached cells. Although the majority of biofilm cells can be killed by antibiotics, surviving persister cells serve as seeds for regrowth of the biofilm after an antibiotic treatment. Furthermore, owing to the extracellular polysaccharide matrix, penetration of antibiotics into the biofilm is hindered and the access to the cells is reduced. Thus, the persister cells and exopolysaccharide matrix play important roles in biofilm-associated drug resistance.

It has been observed that the clinical isolates of *Pseudomonas aeruginosa* in the airways of cystic fibrosis patients produces more biofilm-like microcolonies, harboring drug tolerant persister cells. The dormancy and antibiotic tolerance of persister cells and their capabilities to relapse to normal cells pose a major therapeutic challenge to the treatment of infectious diseases (10). To address this grand challenge, it is important to develop new therapies that can reduce the antibiotic tolerance of persister cells.

During bacterial infection, the human immune system coordinates many types of cells and molecules to eliminate the invading pathogen. The host innate immunity acts as the first line of defense to block the entry of pathogens and kill the microbes that successfully penetrate the epithelial barrier. Innate immune system also activates the adaptive immunity, that is more specific against the invading species and provides long-term protection by developing antibodies and memory lymphocytes. During innate immune response, macrophages and dendritic cells secrete cytokines, which are signaling proteins acting as mediators to attract more immune cells, such as phagocytes. The cytokines can be classified into subgroups such interleukins, tumor necrosis factors, interferons, colony simulating factors, transforming growth factors and chemokines. These cytokines have important functions in regulating the host responses to infections and inflammations. Macrophages secrete various cytokines like IL-1, IL-6, IL-8, IL-10, IL-11, IL-12, IL-15 TNF-α, IFN-α, -β, M-CSF, GM-CSF, G-CSF, etc. Among them, GM-CSF (granulocyte macrophage-colony stimulating factor), secreted by macrophages in response to microbial pathogens, participates in the survival and activation of macrophages, neutrophils, eosinophils and maturation of dendritic cells. Increase in the level of GM-CSF helps recruit monocytes/macrophages to the sites of infection. The receptor for GM-CSF, CD116 is expressed on the hematopoietic cells and is composed of specific α chain and β chain. GM-CSF binds to the α chain with low affinity, but binding to the β chain causes dimerization of both α and β subunits. This dimerization increases the binding affinity of GM-CSF to its receptor, which leads to receptor activation resulting in stimulation of JAK2 (Janus Kinase 2) pathway. The JAK2 protein is for controlling the production of blood cells from hematopoietic stem cells. It is observed that under normal conditions, the level of GM-CSF in the circulation is below 0.35 pM, but it increases as a response to *P. aeruginosa* lipopolysaccharide (LPS), which is a major component of the outer membrane of this microbe and contributes to its virulence. The response of alveolar macrophage to LPS purified from *P. aeruginosa* in (GM-CSF)-deficient ($GM^{-/-}$) and wild type ($GM^{+/+}$) mice has been studied, and it was observed that GM-CSF is required for the alveolar macrophage response to LPS by stimulating expression of a specific subset of components of the Toll-like receptor 4 (TLR-4). TLR-4 is a protein which detects the LPS of Gram-negative bacteria.

Description of the Related Art Section Disclaimer: To the extent that specific patents/publications are discussed above in this Description of the Related Art Section or elsewhere in this Application, these discussions should not be taken as an admission that the discussed patents/publications are prior art for patent law purposes. For example, some or all of the discussed patents/publications may not be sufficiently early in time, may not reflect subject matter developed early enough in time and/or may not be sufficiently enabling so as to amount to prior art for patent law purposes. To the extent that specific patents/publications are discussed above in this Description of the Related Art Section and/or throughout the application, they are all hereby incorporated by reference into this document in their respective entirety(ies).

SUMMARY OF THE INVENTION

Various embodiments of the present invention may be advantageous in that they may solve or reduce one or more of the potential problems and/or disadvantages discussed above.

It is therefore a principal object and advantage of the present invention to address the great challenge to treatment of infectious diseases caused by persister cells. Compared to the well documented studies on cytokine production and the functions of cytokines in stimulating immune cells, there is little knowledge about their direct effects on bacteria. The effects of cytokines on antibiotic tolerant persister cells have not been studied.

In accordance with the foregoing principal object and advantage and as described further in the Detailed Description section herein, an embodiment of the present invention relates to a system and method for controlling and reducing the antibiotic tolerance of bacterial persister cells with host immune factors. Host immune factors can include, but are not limited to, cytokines such as IL-1, IL-6, IL-8, IL-10, IL-11, IL-12, IL-15 TNF-α, IFN-α, -β, M-CSF, GM-CSF, G-CSF etc. (see, e.g., Cavaillon, J. M. 1994. Cytokines and macrophages. Biomed Pharmacother 48:445-453). The host immune factor can be introduced directly to a bacterial species of interest by itself, or can be introduced to a bacterial species of interest with a predetermined antimicrobial, e.g., antibiotic or a mixture of multiple antibiotics.

As further set forth in the detailed description section below, GM-CSF was selected as a representative cytokine and demonstrated its ability to eliminate bacterial persister cells. *P. aeruginosa* was selected as the model bacterium because it well known to form persister cells and biofilms. Effects of GM-CSF on *P. aeruginosa* PAO1 and the mucoid strain PDO300 were compared with the factor introduced alone or with an antibiotic together to test the synergy. PDO300 is a mucA22 mutant (due to a single base pair deletion) of *P. aeruginosa* PAO1, which overproduces the exopolysaccharide alginate. Alginate overproduction leads to mucoidity, which is commonly seen in late stage of cystic fibrosis patients with multidrug tolerant infections. The most upregulated proteins in the mucA22 strain are phosphomannose isomerase (AlgA) and GDP-mannose dehydrogenase (AlgD), which are enzymes involved in alginate biosynthesis; and both are encoded by the algD operon. The alginate overproduction by mucoid *P. aeruginosa* makes the biofilms thicker, which hinders the penetration of antibiotics and reduces the phagocytic activity of the macrophages. To test the antibiotic synergy with the factor, four antibiotics were selected including ciprofloxacin, tobramycin, tetracycline and gentamicin. These antibiotics were selected based on their common use in the treatment of *P. aeruginosa* infections.

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 1:
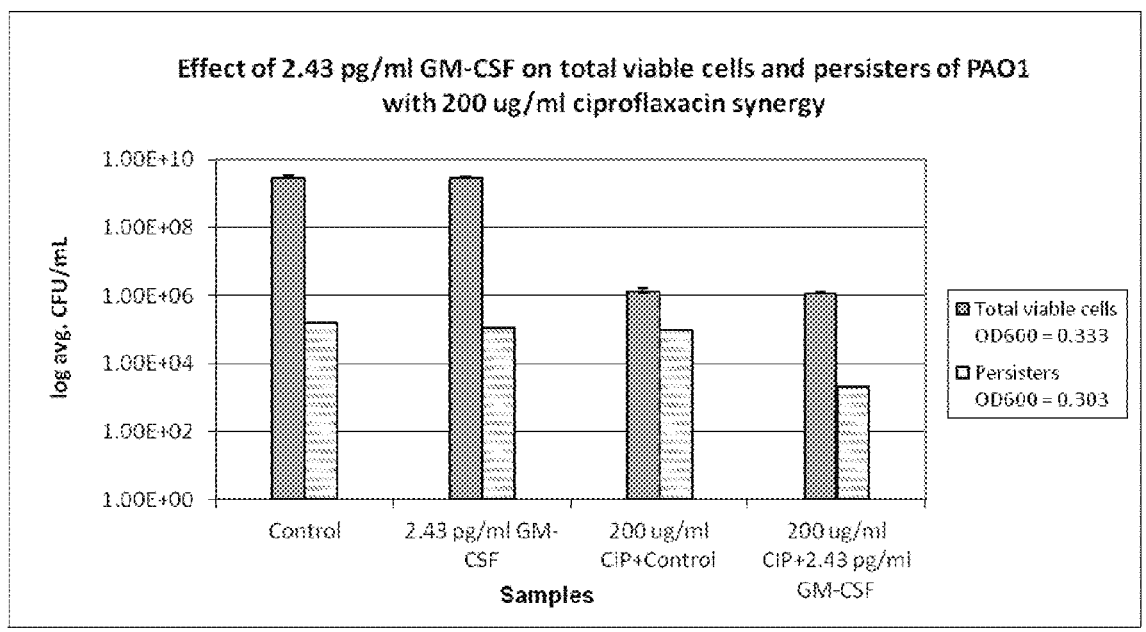
FIG. 1 is a graphical illustration showing the effect of 2.43 pg/mL GM-CSF on total number of viable cells and persisters of planktonic PAO1 as well as synergy with 200 μg/mL ciprofloxacin, in accordance with an embodiment of the present invention.

The present invention will be more fully understood and appreciated by reading the following Detailed Description in conjunction with the accompanying drawings, wherein like reference numerals refer to like components.

Advantages of the invention are illustrated by the Examples section below. However, the particular materials and amounts thereof recited in these examples, as well as other conditions and details, are to be interpreted to apply broadly in the art and should not be construed to unduly restrict or limit the invention in any way. The objective of the experiments detailed in the Examples is to test the hypothesis that host immune factors can help eliminate bacterial persister cells.

During bacterial infections, the innate immune defense of the body is activated and offers the first line of defense against the invading pathogen. The adaptive immune defense is then activated by the innate immune defense and acts as a second line of defense, protecting against future invasions by the same pathogen. The immune system has a variety of cells called leukocytes, which have their individual functions during immune defense. Macrophages are an important type of leukocytes, which are phagocytic and function as a part of innate immune defense and also activate the adaptive immune defense.

The macrophages and other leukocytes secrete cytokines in response to microbial infection. These cytokines are proteins acting as mediators between different immune cells. Macrophages secrete various cytokines such as IL-1, IL-6, IL-8, IL-10, IL-11, IL-12, IL-15 TNF-$\alpha$, IFN-$\alpha$, -$\beta$, M-CSF, GM-CSF, G-CSF etc. Each cytokine has its specific function and is secreted under particular circumstances. For example, GM-CSF (granulocyte macrophage-colony stimulating factor) is secreted by macrophages during pathogenic invasion, participates in the survival and activation of leukocytes like macrophages, neutrophils, eosinophils and maturation of dendritic cells.

As discussed below, experiments were conducted to understand the effects of a representative host immune factor, GM-CSF, on the planktonic and biofilm cells of $P.$ $aeruginosa$ PAO1, PDO300 and $Escherichia$ $coli$ K12, with the factor introduced directly or with an antibiotic together to test the synergy. PDO300 is a mucA22 derivative of PAO1, which overproduces the exopolysaccharide alginate. In cystic fibrosis patients with chronic infection of $P.$ $aeruginosa$, this bacterium tends to convert into a mucoid phenotype as PDO300 exhibits, leading to overproduction of alginate, which makes the biofilm highly resistant to antibiotics. In comparison, $E.$ $coli$ K12, a harmless laboratory strain, was used to compare the effect of GM-CSF on non-pathogenic bacteria. To test the antibiotic synergy with the factor, four antibiotics were selected including ciprofloxacin, tobramycin, tetracycline and gentamicin. These antibiotics were selected because they have been used in the treatment of $P.$ $aeruginosa$ infections.

$Pseudomonas$ $aeruginosa$ was chosen as a representative bacterial species to develop new approaches of persister control. $P.$ $aeruginosa$ is a Gram-negative, opportunistic pathogen which causes a variety of infections, especially in humans with compromised immunity. In patients suffering from cystic fibrosis, this bacterium causes chronic infections with high mortality. $P.$ $aeruginosa$ also commonly forms biofilms in disease conditions, which (as discussed above) are complex communities of cells that grow on surfaces and covered by an extracellular matrix secreted by attached cells. Owing to the extracellular polysaccharide matrix, penetration of antibiotics into the biofilm is hindered and the access to the cells is reduced.

EXAMPLES

Bacterial Strains and Growth Media; and GM-CSF

The bacterial strains used in the experiments described herein are $P.$ $aeruginosa$ PAO1, PDO300 and $E.$ $coli$ K12. All overnight cultures were prepared in Luria Bertani medium containing 10 g/L tryptone, 5 g/L yeast extract and 10 g/L NaCl at 37° C. with shaking at 200 rpm. $P.$ $aeruginosa$ PAO1 and PDO300 biofilms were grown in M63 medium containing 2 g/L $(NH_4)_2SO_4$, 13.6 g/L $KH_2PO_4$, 0.5 g $FeSO_4.7H_2O$, 0.2 mg/L $MgSO_4.7H_2O$, 0.3% glucose and 0.5% casamino acids with the pH adjusted to 7.

The GM-CSF stock used in the experiments described herein had 10 µg/mL GM-CSF, dissolved in phosphate buffer saline supplemented with 0.1% BSA (bovine serum albumin).

Example 1

Effects on Planktonic Cells at Exponential Phase and Stationary Phase

This Example describes the treatment of planktonic $P.$ $aeruginosa$ PAO1, PDO300 and $Escherichia$ $coli$ K12, with GM-CSF introduced directly or together with an antibiotic to test the synergy. All experiments were conducted with cells harvested from exponential phase subcultures with an optical density at 600 nm ($OD_{600}$) of 0.3 to 0.4.

In brief, after preparing an overnight culture of the tested strain in 25 ml LB medium, a subculture was prepared with an $OD_{600}$ of 0.01 in 50 mL LB medium. The subculture was incubated at 37° C. with shaking at 200 rpm for 3-4 h, till an $OD_{600}$ of 0.3 to 0.4 was reached. The exponential phase subculture was then divided equally into two centrifuge tubes, each containing 25 mL of the subculture. The subcultures were washed twice with 0.85% NaCl buffer by vortexing and then centrifuging at 4° C., 8000 rpm for 10 min each time. The washed subcultures/cells were resuspended in 25 mL 0.85% NaCl buffer and vortexed gently for 1 min. One of the tubes of subculture was selected for isolation of persisters by adding 200 µg/mL ciprofloxacin (for PAO1 and PDO300 strains) or 100 µg/mL ampicillin (for $E.$ $coli$ K12 strain). After adding the antibiotic for persister isolation, the subculture was incubated at 37° C., shaking at 200 rpm for 3.5 h.

To test the effects of GM-CSF on viability of persisters, the second tube was used to quantify the total number of viable cells and 1 mL of the washed persister cells was divided into 6 microcentrifuge tubes; 3 were control and the other 3 were GM-CSF treatment samples. In the treatment samples, GM-CSF was added to a concentration of 2.43 pg/mL (or 0.17 pM), the same as found in healthy human bodies. The control samples were supplemented with the same concentration of PBS and BSA as present in 2.43 pg/mL (or 0.17 pM) GM-CSF samples.

After incubating at 37° C. for 1 h with shaking at 200 rpm, the samples were plated on LB agar plates (15 g/L bacto agar) using drop plate method. The agar plates were then incubated for 24 h at 37° C. to count the total number of persister cells and understand the effect of 0.17 pM GM-CSF on the viability of persister cells.

To test the synergy with antibiotics, the above samples were then incubated at 37° C. for 3.5 h with shaking at 200 rpm after adding the selected antibiotic. After 3.5 h, the CFU of samples was quantified in the same way to understand if there is any synergy between GM-CSF and antibiotic. Similar treatments were performed on the total population in exponential phase as well. Apart from exponential phase, the synergistic effects of GM-CSF with antibiotics on total viable cells and persisters were also evaluated at stationary phase but PBS buffer (pH=7.4) was used in the experiments instead of 0.85% NaCl solution. Moreover, the 1 h and 3.5 h treatments were performed as co-treatments.

Example 2

Effects of GM-CSF on Planktonic *P. aeruginosa* PAO1 Cells

After treatment of planktonic PAO1 cells with 2.43 pg/ml GM-CSF, the results show that the average CFU/mL of total viable cells was reduced by 15.38%, 34.62%, 23.06% and 10.53% with 200 μg/mL ciprofloxacin, 200 μg/mL tobramycin, 200 μg/mL tetracycline and 200 μg/mL gentamicin, respectively. The average CFU/mL of persisters was reduced by 97.95%, 81.42%, 65.66% and 59.31% with 200 μg/mL ciprofloxacin, 200 μg/mL tobramycin, 200 μg/mL tetracycline and 200 μg/mL gentamicin, respectively. Thus, this factor was found to have cidal effects on both regular and persister cells of PAO1. The effects were dramatically enhanced in the presence of some antibiotics, especially ciprofloxacin and tobramycin, clearly a synergistic effect.

FIG. 1 is a graphical illustration showing the effect of 2.43 pg/mL GM-CSF on total number of viable cells and persisters of planktonic PAO1 as well as synergy with 200 μg/mL ciprofloxacin. A summary results table (Table 1) is provided below:

TABLE 1

Summary:

| Samples | % change in avg. CFU/ml after adding factor | % change in avg. CFU/ml after adding factor + CIP |
| --- | --- | --- |
| Total viable cells | −2.22% | −15.38% |
| Persisters | −28.19% | −97.95% |

Figure 2:
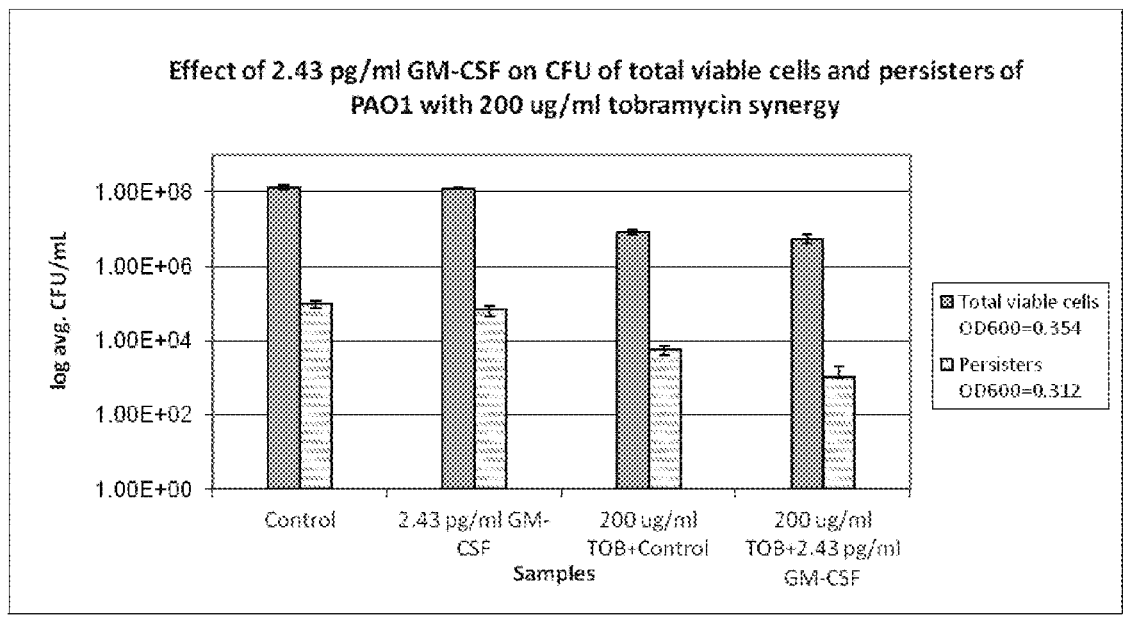
FIG. 2 is a graphical illustration showing the effect of 2.43 pg/ml GM-CSF on the total number of viable cells and persisters of planktonic PAO1 and synergy with 200 μg/mL tobramycin, in accordance with an embodiment of the present invention.

FIG. 2 is a graphical illustration showing the effect of 2.43 pg/ml GM-CSF on the total number of viable cells and persisters of planktonic PAO1 and synergy with 200 μg/mL tobramycin. A summary results table (Table 2) is provided below:

TABLE 2

Summary:

| Samples | % change in avg. CFU/ml after adding factor | % change in avg. CFU/ml after adding factor + TOB |
| --- | --- | --- |
| Total viable cells | −5.00% | −34.62% |
| Persisters | −27.40% | −81.42% |

Figure 3:
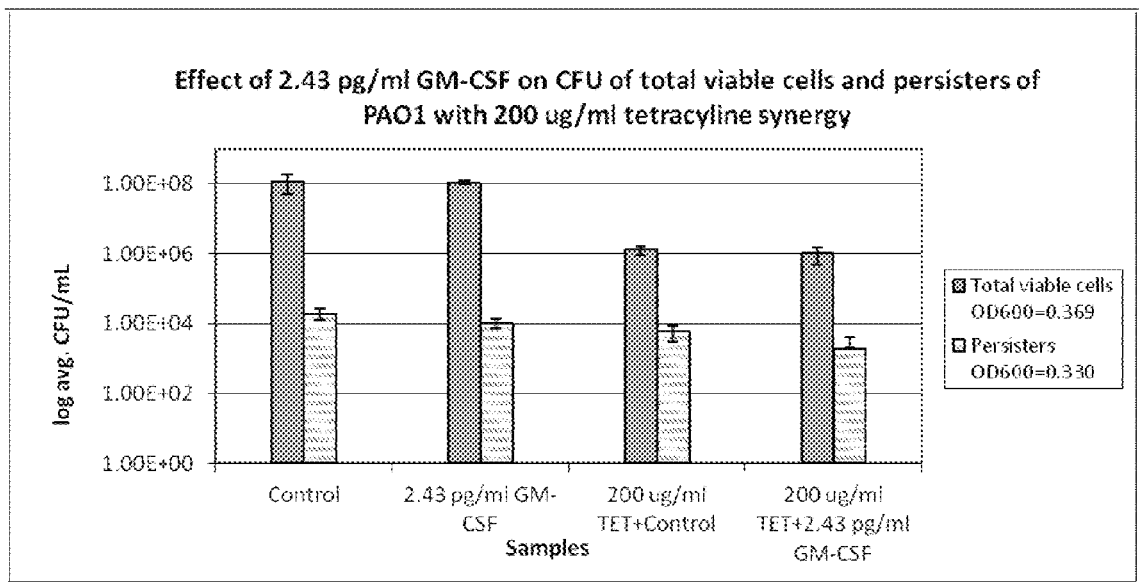
FIG. 3 is a graphical illustration showing the effect of 2.43 pg/ml GM-CSF on the total viable cells and persisters of planktonic PAO1 and synergy with 200 μg/ml tetracycline, in accordance with an embodiment of the present invention.

FIG. 3 is a graphical illustration showing the effect of 2.43 pg/ml GM-CSF on the total viable cells and persisters of planktonic PAO1 and synergy with 200 μg/ml tetracycline. A summary results table (Table 3) is provided below:

TABLE 3

Summary:

| Samples | % change in avg. CFU/ml after adding factor | % change in avg. CFU/ml after adding factor + TET |
| --- | --- | --- |
| Total viable cells | −2.94% | −23.08% |
| Persisters | −44.12% | −65.66% |

Figure 4:
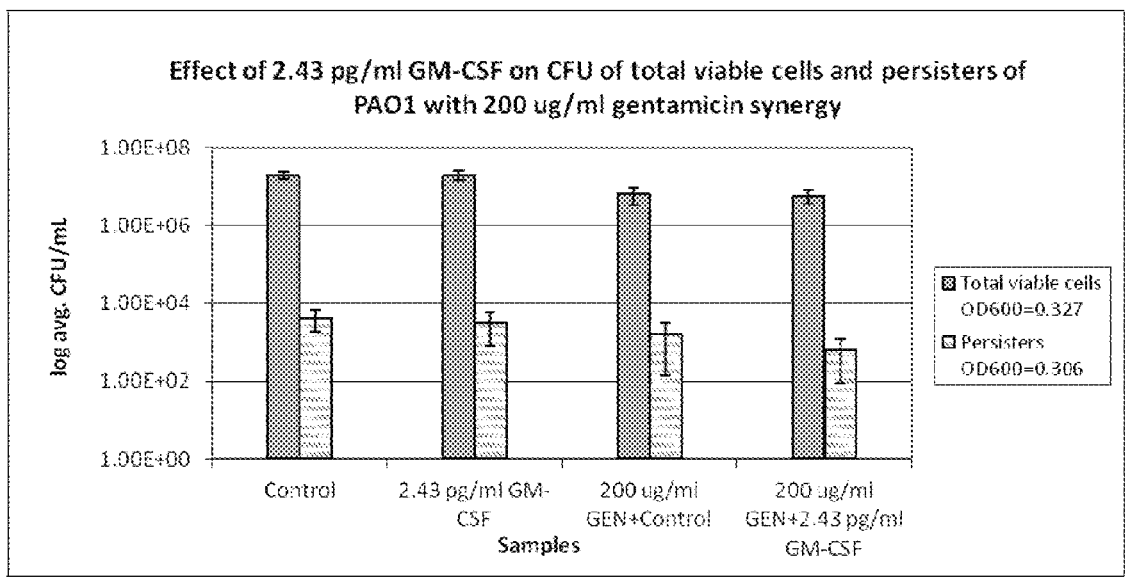
FIG. 4 is a graphical illustration showing the effect of 2.43 pg/mL GM-CSF on the total viable cells and persisters of planktonic PAO1 as well as synergy with 200 μg/mL gentamicin, in accordance with an embodiment of the present invention.

FIG. 4 is a graphical illustration showing the effect of 2.43 pg/mL GM-CSF on the total viable cells and persisters of planktonic PAO1 as well as synergy with 200 μg/mL gentamicin. A summary results table (Table 4) is provided below:

TABLE 4

Summary:

| Samples | % change in avg. CFU/ml after adding factor | % change in avg. CFU/ml after adding factor + GEN |
| --- | --- | --- |
| Total viable cells | −1.69% | −10.53% |
| Persisters | −21.75% | −59.31% |

As shown in Tables 1-4 above and in Tables 5-8 below, GM-CSF sensitized PAO1 cells to different antibiotics (ciprofloxacin, tobramycin, gentamycin and tetracycline). GM-CSF was found to be effective against both regular cells and persister cells. However, GM-CSF is more effective against persister cells. Since persisters are highly tolerant to antibiotics, these results are intriguing for developing more effective therapies.

Table 5 summarizes the effects of 0.17 pM, 1.7 and 17 pM GM-CSF on the total population and persister cells of PAO1 at stationary phase treated with 200 μg/mL ciprofloxacin.

TABLE 5

| | % change in avg. CFU/mL by GM-CSF (compared to GM-CSF free control) | |
| --- | --- | --- |
| Samples | 1.7 pM | 17 pM |
| Total viable cells | −19.5 ± 15.6% | −10.3 ± 21.5% |
| Persisters | −53.8 ± 16.1% | −74.0 ± 2.9% |

Table 6 summarizes the effects of 0.17 pM, 1.7 and 17 pM GM-CSF on the total population and persister cells of PAO1 at stationary phase treated with 200 μg/mL tobramycin.

TABLE 6

| | % change in avg. CFU/mL by GM-CSF (compared to GM-CSF free control) | |
| --- | --- | --- |
| Samples | 1.7 pM | 17 pM |
| Total viable cells | −9.4 ± 20.0% | +3.1 ± 18.6% |
| Persisters | −82.7 ± 2.3% | −86.5 ± 1.7% |

Table 7 summarizes the effects of 0.17 pM, 1.7 and 17 pM GM-CSF on the total population and persister cells of PAO1 at stationary phase treated with 200 μg/mL tetracycline.

TABLE 7

| Samples | % change in avg. CFU/mL by GM-CSF (compared to GM-CSF free control) 17 pM |
|---|---|
| Total viable cells | −1.0 ± 12.4% |
| Persisters | −91.2 ± 3.2% |

Table 8 summarizes the effects of 0.17 pM, 1.7 and 17 pM GM-CSF on the total population and persister cells of PAO1 at stationary phase treated with 200 μg/mL gentamicin.

TABLE 8

| Samples | % change in avg. CFU/mL by GM-CSF (compared to GM-CSF free control) | |
|---|---|---|
|  | 1.7 pM | 17 pM |
| Total viable cells | −13.1 ± 7.4% | −15.9 ± 7.4% |
| Persisters | −12.7 ± 8.8% | −25.4 ± 10.6% |

Example 3

Effects of GM-CSF on Planktonic *P. aeruginosa* PDO300 Cells

After adding 2.43 pg/ml GM-CSF to planktonic PDO300 cells, the results show that the average CFU/ml of total viable cells was reduced by 25.00%, 8.33%, 12.50% and 20.00% in the presence of 50 μg/mL ciprofloxacin, 50 μg/mL tobramycin, 50 μg/mL tetracycline and 200 μg/mL gentamicin, respectively. The average CFU/ml of persisters was reduced by 27.78%, 75.86%, 32.69% and 50.94% in the presence of 50 μg/mL ciprofloxacin, 50 μg/mL tobramycin, 50 μg/mL tetracycline and 200 μg/mL gentamicin, respectively.

Figure 5:
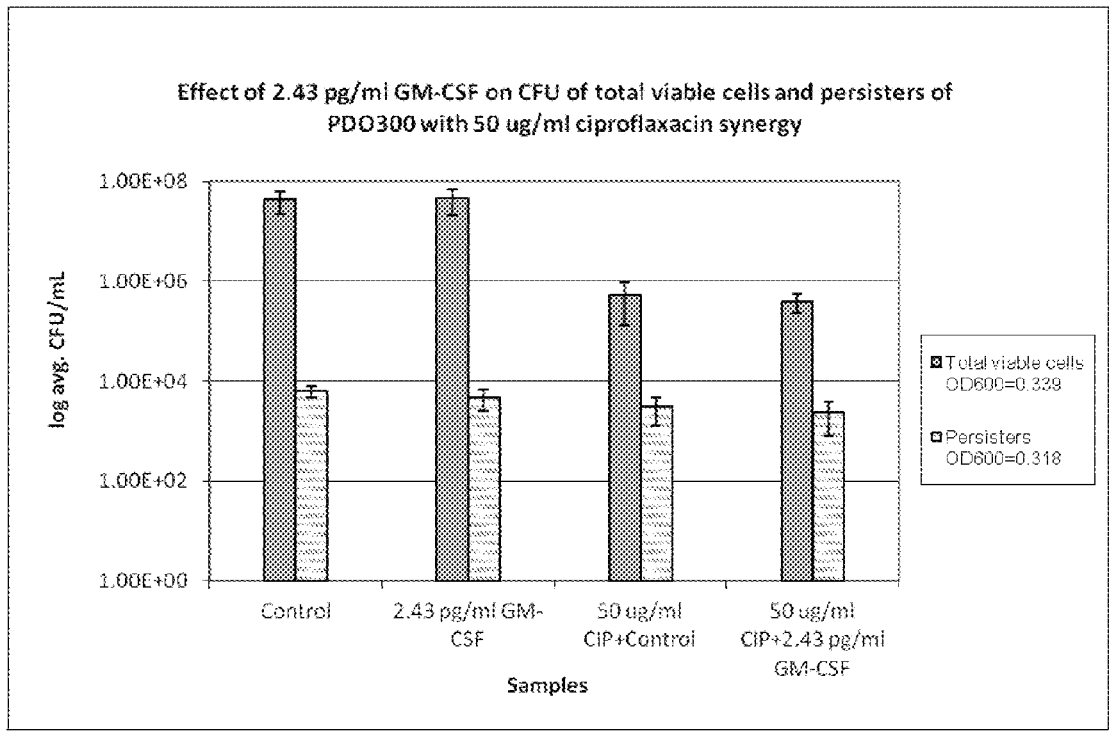
FIG. 5 is a graphical illustration showing the effect of 2.43 pg/mL GM-CSF on the total viable cells and persisters of planktonic PDO300 and synergy with 50 μg/mL ciprofloxacin, in accordance with an embodiment of the present invention.

FIG. 5 is a graphical illustration showing the effect of 2.43 pg/mL GM-CSF on the total viable cells and persisters of planktonic PDO300 and synergy with 50 μg/mL ciprofloxacin. A summary results table (Table 9) is provided below:

TABLE 9

Summary:

| Samples | % change in avg. CFU/ml after adding factor | % change in avg. CFU/ml after adding factor + CIP |
|---|---|---|
| Total viable cells | +7.69% | −25.00% |
| Persisters | −31.58% | −27.78% |

Figure 6:
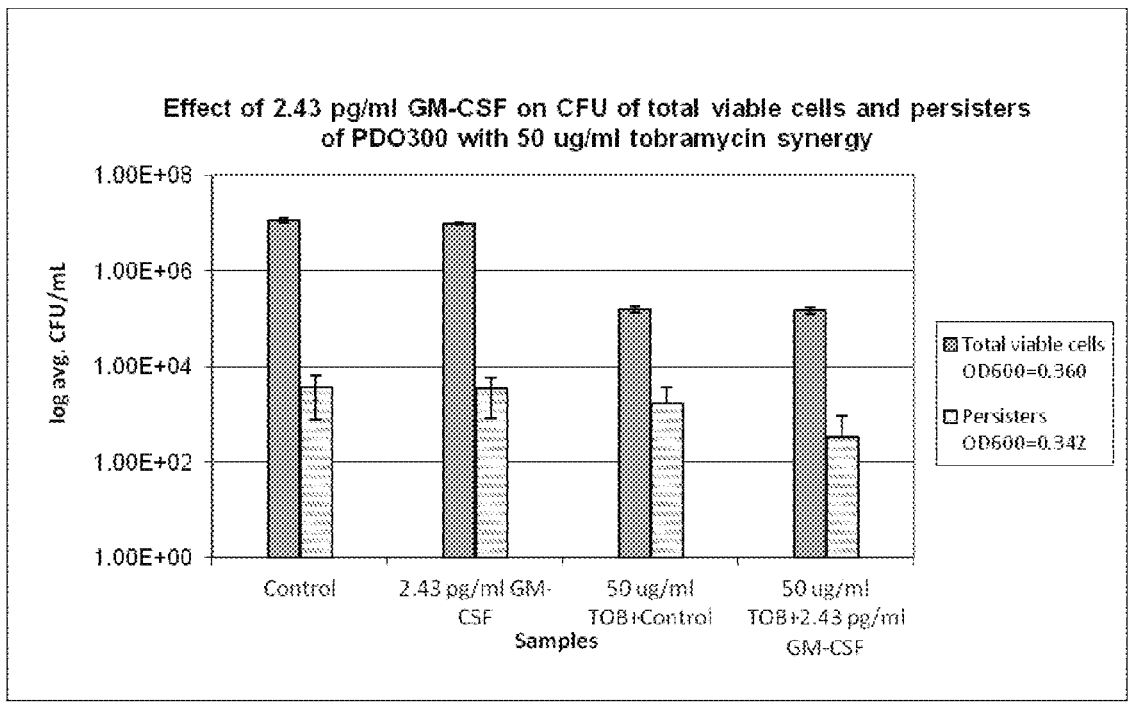
FIG. 6 is a graphical illustration showing the effect of 2.43 pg/mL GM-CSF on the total viable cells and persisters of planktonic PDO300 as well as synergy with 50 μg/mL tobramycin, in accordance with an embodiment of the present invention.

FIG. 6 is a graphical illustration showing the effect of 2.43 pg/mL GM-CSF on the total viable cells and persisters of planktonic PDO300 as well as synergy with 50 μg/mL tobramycin. A summary results table (Table 10) is provided below:

TABLE 10

Summary:

| Samples | % change in avg. CFU/ml after adding factor | % change in avg. CFU/ml after adding factor + TOB |
|---|---|---|
| Total viable cells | −17.14% | −8.33% |
| Persisters | +9.72% | −75.86% |

Figure 7:
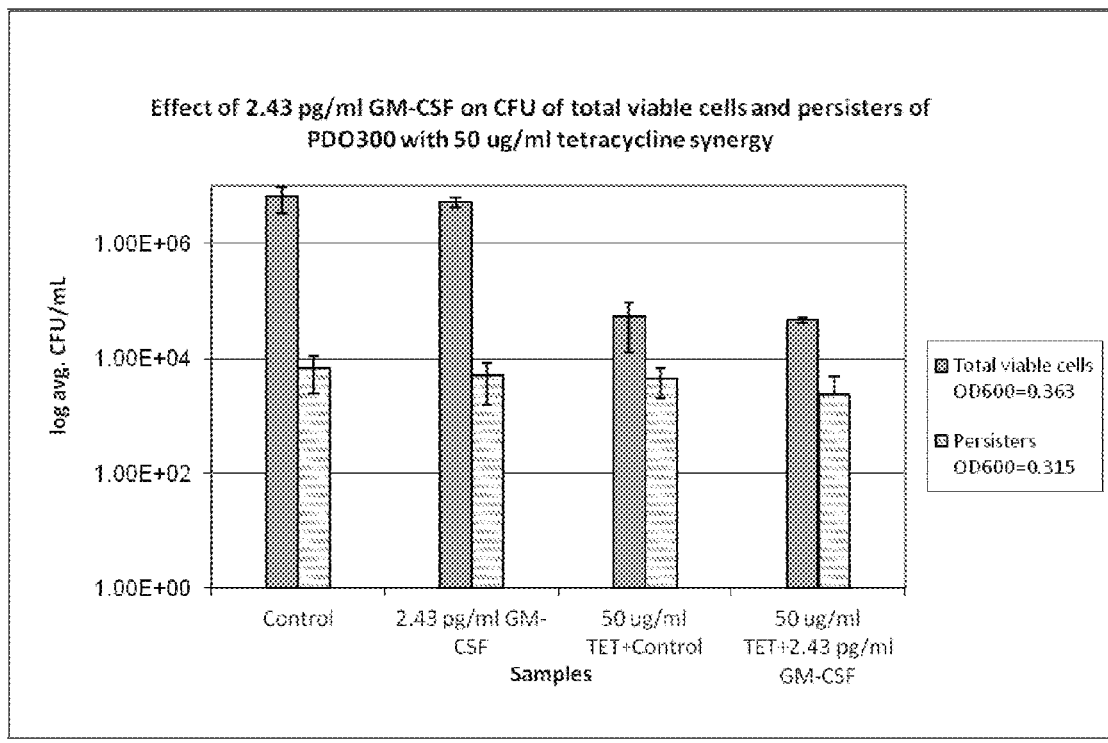
FIG. 7 is a graphical illustration showing the effect of 2.43 pg/mL GM-CSF on the total population and persisters of planktonic PDO300 as well as synergy with 50 μg/mL tetracycline, in accordance with an embodiment of the present invention.

FIG. 7 is a graphical illustration showing the effect of 2.43 pg/mL GM-CSF on the total population and persisters of planktonic PDO300 as well as synergy with 50 μg/mL tetracycline. A summary results table (Table 11) is provided below:

TABLE 11

Summary:

| Samples | % change in avg. CFU/ml after adding factor | % change in avg. CFU/ml after adding factor + TET |
|---|---|---|
| Total viable cells | −20.00% | −12.50% |
| Persisters | −6.25% | −32.69% |

Figure 8:
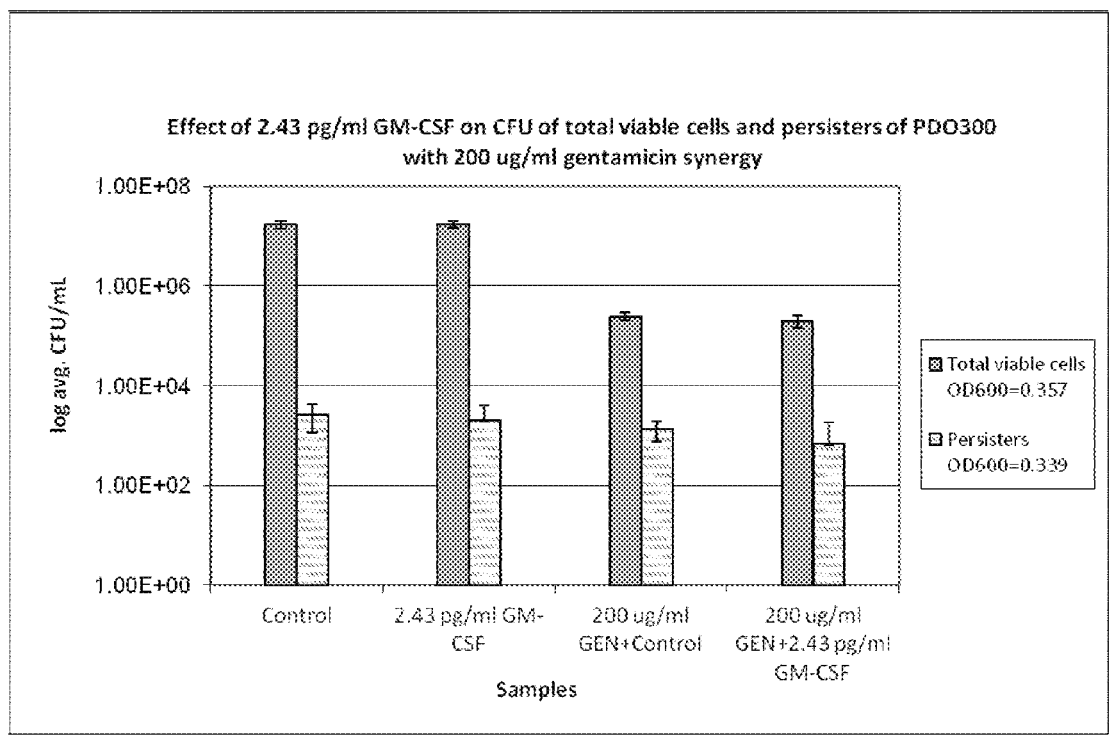
FIG. 8 is a graphical illustration showing the effect of 2.43 pg/mL GM-CSF on the total population and persisters of planktonic PDO300 and synergy with 200 μg/ml gentamicin, in accordance with an embodiment of the present invention.

FIG. 8 is a graphical illustration showing the effect of 2.43 pg/mL GM-CSF on the total population and persisters of planktonic PDO300 and synergy with 200 μg/ml gentamicin. A summary results table (Table 12) is provided below:

TABLE 12

Summary:

| Samples | % change in avg. CFU/ml after adding factor | % change in avg. CFU/ml after adding factor + GEN |
|---|---|---|
| Total viable cells | 1.92% | −20.00% |
| Persisters | −26.42% | −50.94% |

As shown herein, similar to the data of PAO1, this immune factor was also found to sensitize the cells of this mucoid strain to some antibiotics, e.g., Tob and Gen (Tables 10 and 12).

Table 13 below summarizes the effects of 0.17 pM GM-CSF on the total population and persister cells of PDO300 at exponential phase with and without 50 μg/mL ciprofloxacin, 50 μg/mL tobramycin, 50 μg/mL tetracycline, 50 μg/mL gentamycin.

TABLE 13

| Samples | % change in avg. CFU/mL by GM-CSF (compared to GM-CSF free control) | | | |
|---|---|---|---|---|
|  | With 50 μg/mL Cip | With 50 μg/mL Tob | With 50 μg/mL Tet | With 200 μg/mL Gen |
| Total viable cells | −25.0% | −8.3% | −12.5% | −20.0% |
| Persisters | −22.2±% | −80.0% | −46.2% | −50.0% |

Example 4

Effects of GM-CSF on Planktonic *E. coli* K12 Cells

After adding 2.43 pg/ml GM-CSF to planktonic *E. coli* K12 cells, the results show that the average CFU/ml of total viable cells was changed by +5.88%, −32.00%, −19.05% and −31.34% in the presence of 2 μg/mL ciprofloxacin, 70 μg/mL tobramycin, 20 μg/mL tetracycline and 200 μg/mL gentamicin, respectively. The average CFU/mL of persisters changed by −6.18%, +11.16%, +12.00% and +18.52% with 2 μg/mL ciprofloxacin, 70 μg/mL tobramycin, 20 μg/mL tetracycline and 200 μg/mL gentamicin, respectively.

Figure 9:
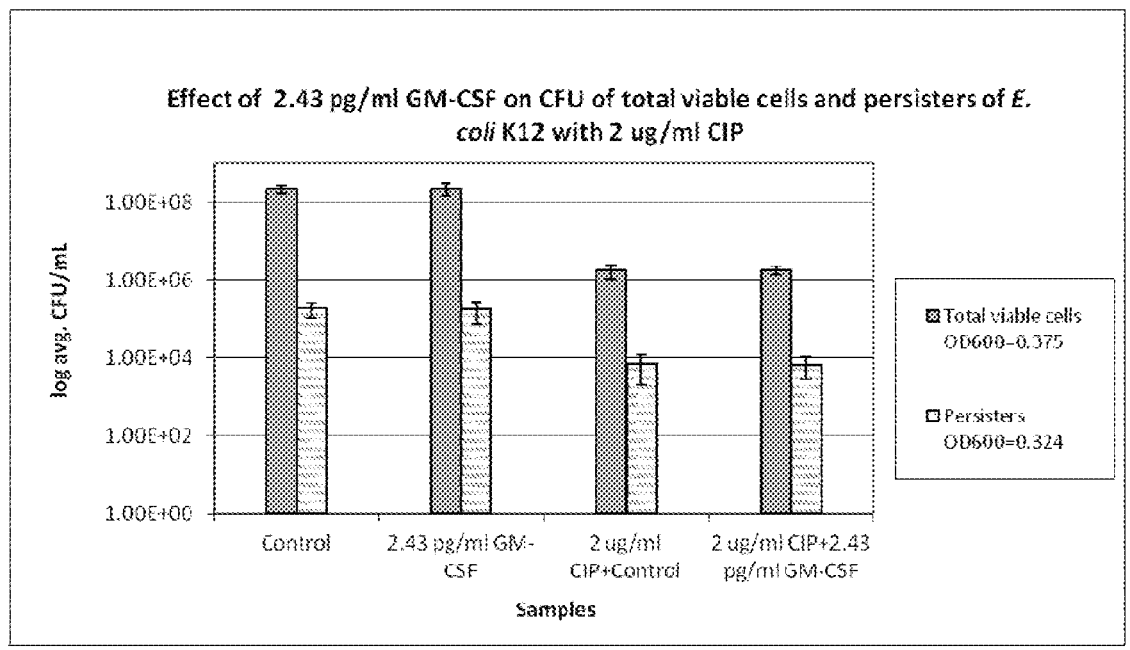
FIG. 9 is a graphical illustration showing the effect of 2.43 pg/mL GM-CSF on the total population and persisters of planktonic *E. coli* K12 and synergy with 2 μg/mL ciprofloxacin, in accordance with an embodiment of the present invention.

FIG. 9 is a graphical illustration showing the effect of 2.43 pg/mL GM-CSF on the total population and persisters of planktonic *E. coli* K12 and synergy with 2 µg/mL ciprofloxacin. A summary results table (Table 14) is provided below:

TABLE 14

Summary:

| Samples | % change in avg. CFU/ml after adding factor | % change in avg. CFU/ml after adding factor + CIP |
|---|---|---|
| Total viable cells | +1.52% | +5.88% |
| Persisters | −8.53% | −6.18% |

Figure 10:
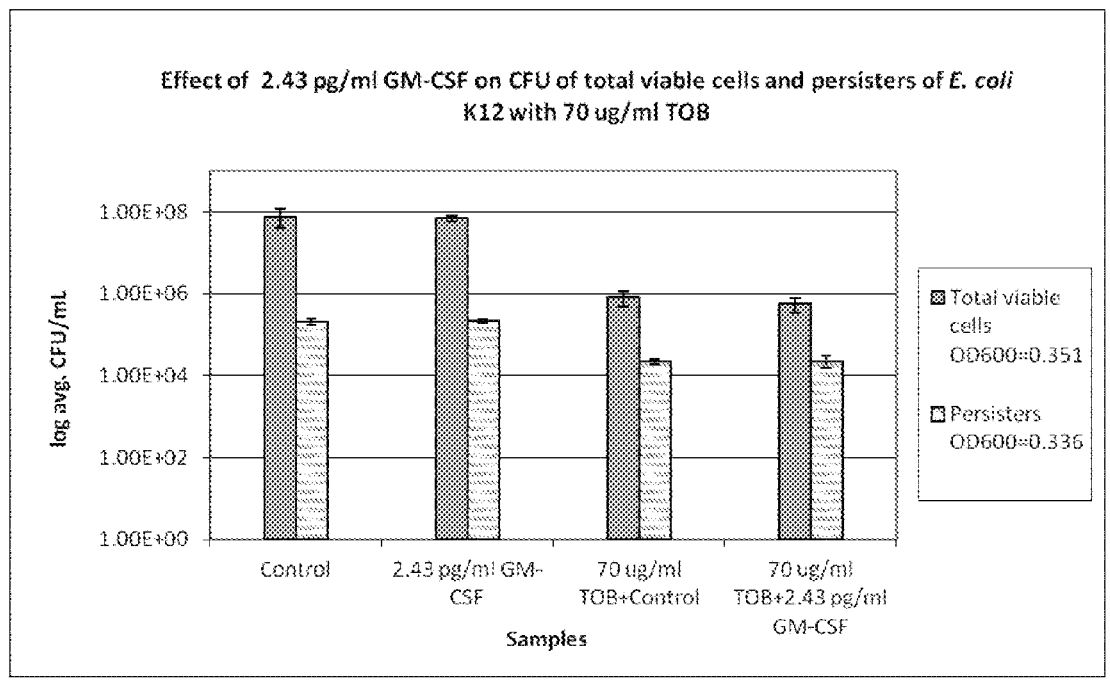
FIG. 10 is a graphical illustration showing the effect of 2.43 pg/mL GM-CSF on the total population and persisters of planktonic *E. coli* K12 and synergy with 70 μg/mL tobramycin, in accordance with an embodiment of the present invention.

FIG. 10 is a graphical illustration showing the effect of 2.43 pg/mL GM-CSF on the total population and persisters of planktonic *E. coli* K12 and synergy with 70 µg/mL tobramycin. A summary results table (Table 15) is provided below:

TABLE 15

Summary:

| Samples | % change in avg. CFU/ml after adding factor | % change in avg. CFU/ml after adding factor + TOB |
|---|---|---|
| Total viable cells | −8.70% | −32.00% |
| Persisters | +11.26% | +11.16% |

Figure 11:
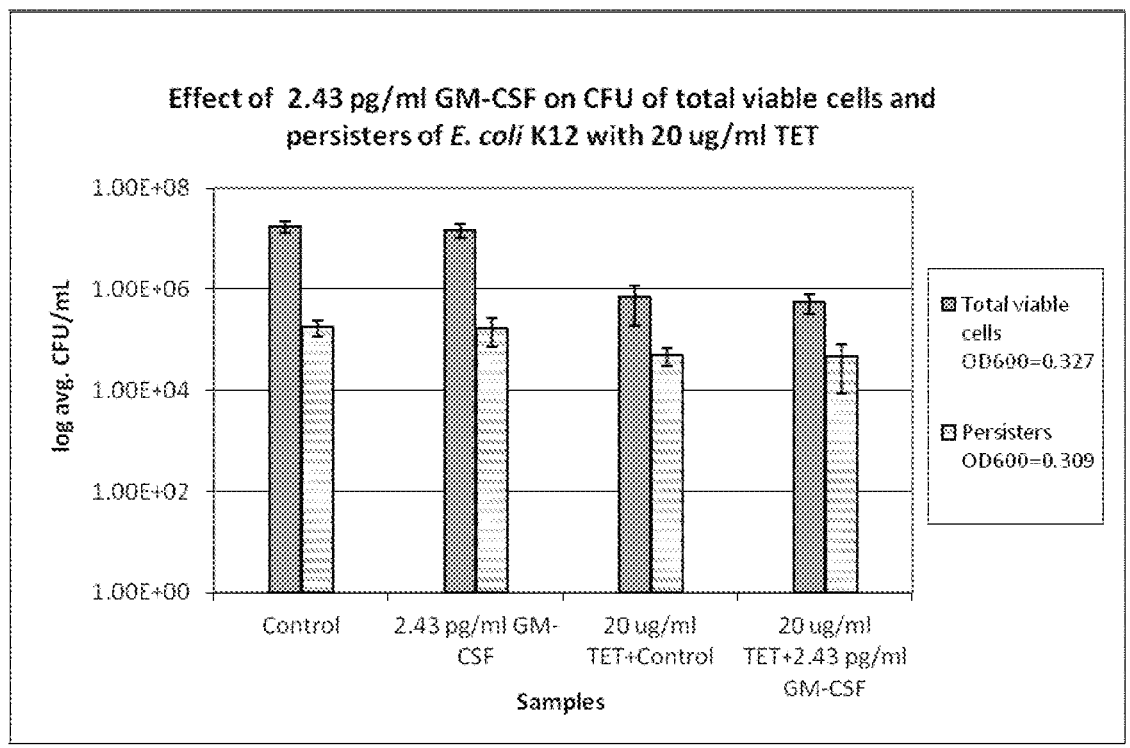
FIG. 11 is a graphical illustration showing the effect of 2.43 pg/mL GM-CSF on the total population and persisters of planktonic *E. coli* K12 and synergy with 20 μg/mL tetracycline, in accordance with an embodiment of the present invention.

FIG. 11 is a graphical illustration showing the effect of 2.43 pg/mL GM-CSF on the total population and persisters of planktonic *E. coli* K12 and synergy with 20 µg/mL tetracycline. A summary results table (Table 16) is provided below:

TABLE 16

Summary:

| Samples | % change in avg. CFU/ml after adding factor | % change in avg. CFU/ml after adding factor + TET |
|---|---|---|
| Total viable cells | −16.67% | −19.05% |
| Persisters | +17.78% | +12.00% |

Figure 12:
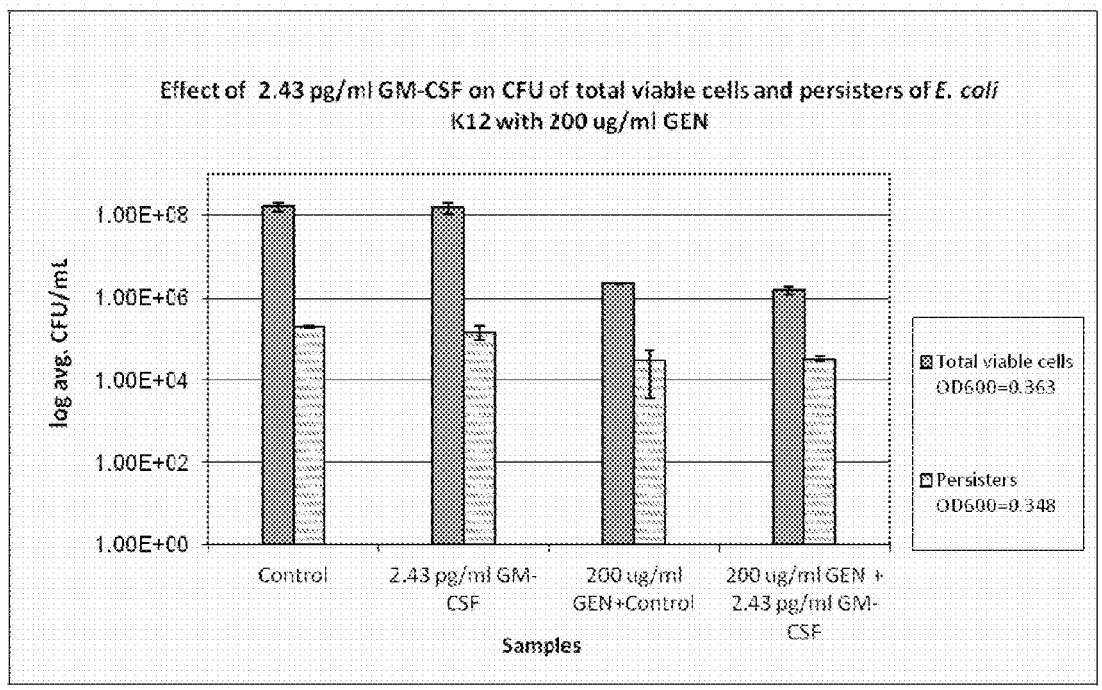
FIG. 12 is a graphical illustration showing the effect of 2.43 pg/mL GM-CSF on the total population and persisters of planktonic *E. coli* K12 and synergy with 200 μg/mL gentamicin, in accordance with an embodiment of the present invention.

FIG. 12 is a graphical illustration showing the effect of 2.43 pg/mL GM-CSF on the total population and persisters of planktonic *E. coli* K12 and synergy with 200 µg/mL gentamicin. A summary results table (Table 17 is provided below:

TABLE 17

Summary:

| Samples | % change in avg. CFU/ml after adding factor | % change in avg. CFU/ml after adding factor + GEN |
|---|---|---|
| Total viable cells | −6.25% | −31.34% |
| Persisters | −17.81% | +18.52% |

As shown herein, compared to the pathogenic strain *P. aeruginosa*, GM-CSF was found to be ineffective to *E. coli* persister cells.

Table 18 summarizes the effects of 0.17 pM GM-CSF on the total population and persister cells of *E. coli* K12 at exponential phase treated with and without 2 µg/mL ciprofloxacin.

TABLE 18

| | % change in avg. CFU/mL by GM-CSF (compared to GM-CSF free control) | | | |
|---|---|---|---|---|
| Samples | With 2 µg/mL Cip | With 70 µg/mL Tob | Without 20 µg/mL Tet | With 200 µg/mL Gen |
| Total viable cells | +5.9% | −32.0% | −19.0% | −31.3% |
| Persisters | −4.8% | +1.5% | −6.7% | +11.1% |

Example 5

Effects on Biofilms

This Example describes the treatment of biofilms made from *P. aeruginosa* PAO1, PDO300 and *Escherichia coli* K12, with GM-CSF introduced directly or together with an antibiotic to test the synergy.

In brief, after preparing an overnight culture, it was subcultured to an initial $OD_{600}$ of 0.01 to a total volume of 20 mL M63 medium (for PAO1 and PDO300) or 20 ml LB medium (for *E. coli* K12) in a petri dish with 316L stainless steel coupons (1.75 cm×1 cm). The biofilm was grown for 24 h at 37° C. without shaking. After incubation, the coupons were washed by gently dipping in 0.85% NaCl twice using tweezers and were placed in new empty petri dishes.

To test the synergistic effects between GM-CSF (2.43 pg/mL or 0.17 pM) and antibiotics, a total of 8 coupons were analyzed. These 8 coupons were placed in 4 petri dishes (2 coupons in each dish). The two dishes were labeled as control and the other two as treatment samples. In the treatment samples, GM-CSF was added to 20 mL of 0.85% NaCl to a concentration of 2.43 pg/mL (or 0.17 pM). The control samples were supplemented with the same amount of PBS and BSA as present in the samples with 2.43 pg/ml (or 0.17 pM) GM-CSF. The coupons were incubated at 37° C. for 2 h.

After incubation, a control dish and a treatment dish was selected for studying the killing effect of 2.43 pg/ml GM-CSF on biofilm cells. Each coupon after gentle washing with 0.85% NaCl buffer, was placed in a test tube with 3 mL 0.85% NaCl buffer in each. They were sonicated (B200, Sinosonic Industrial Co., Ltd., Taiwan) for 4 mins to release the biofilm cells in the buffer. After vortexing for 1 min, they were plated on LB agar plates using drop plate method. The CFU was counted after incubation at 37° C. for 24 h to count the total number of viable cells. Furthermore, the synergistic effect of antibiotics with GM-CSF was evaluated with additional 3.5 h treatment with antibiotic at 37° C. After incubation, drop plate method was performed and the CFU was counted to understand if there is a synergistic effect.

Example 6

Effects of GM-CSF on *P. aeruginosa* PAO1 Biofilm

After adding 2.43 pg/mL GM-CSF, the results show that the average CFU/ml of biofilm cells was reduced by only 1.3% (average of 2 experiments). In the presence of an antibiotic, the average CFU/mL of biofilm cells was reduced by 22.8%, 33.3%, 7.5% and 10.5% with 200 µg/mL ciprofloxacin, 200 µg/mL tobramycin, 200 µg/mL tetracycline and 250 µg/mL gentamicin, respectively. These results are consistent with those obtained for planktonic cells, but less significant. This is probably due to the presence of the polysaccharide matrix and suggests that the effects may be enhanced by engineering the structures of GM-CSF.

Figure 13:
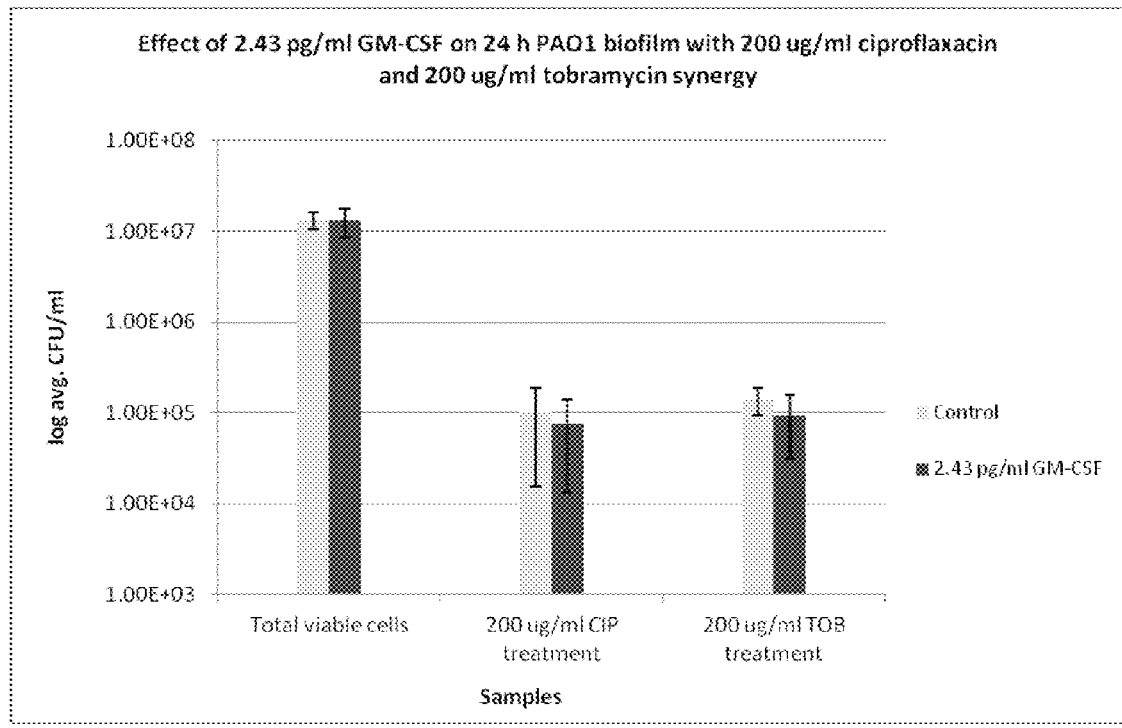
FIG. 13 is a graphical illustration showing the effect of 2.43 pg/ml GM-CSF on 24-h PAO1 biofilm and synergy with 200 μg/mL ciprofloxacin and 200 μg/mL tobramycin, in accordance with an embodiment of the present invention.

FIG. 13 is a graphical illustration showing the effect of 2.43 pg/ml GM-CSF on 24-h PAO1 biofilm and synergy with 200 μg/mL ciprofloxacin and 200 μg/mL tobramycin. A summary results table (Table 19) is provided below:

TABLE 19

Summary:

| % change in avg. CFU/ml of total viable cells | % change in avg. CFU/ml after adding factor + CIP | % change in avg. CFU/ml after adding factor + TOB |
|---|---|---|
| −1.3% | −23.8% | −34.1% |

Figure 14:
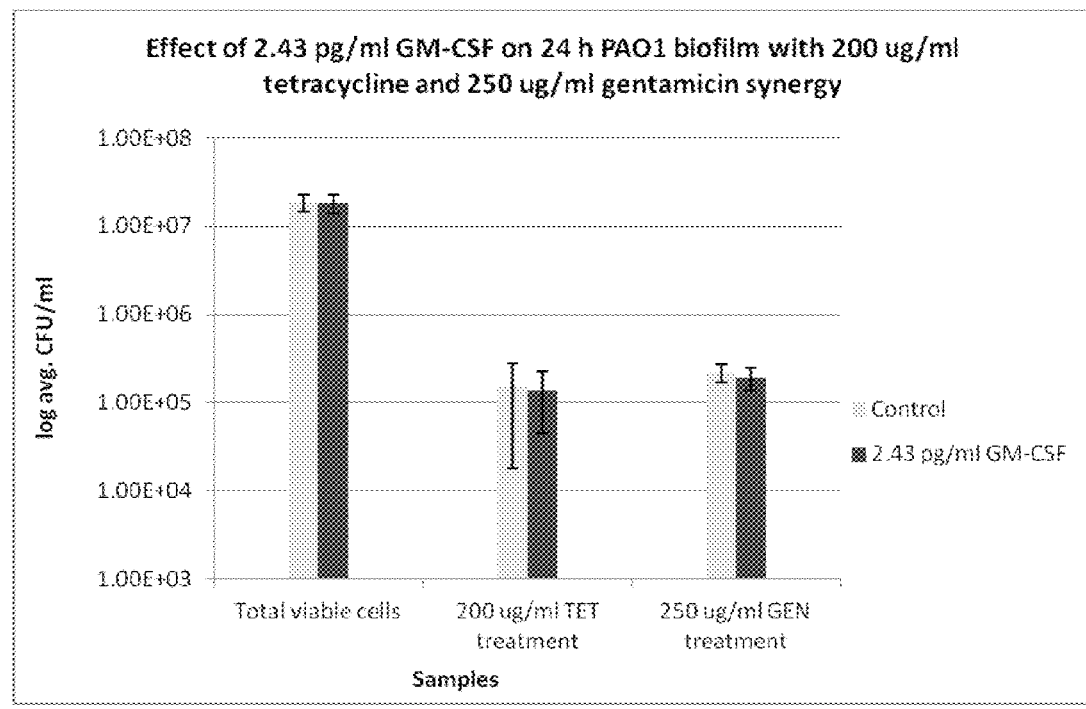
FIG. 14 is a graphical illustration showing the effect of 2.43 pg/mL GM-CSF on 24-h PAO1 biofilm and synergy with 200 μg/mL tetracycline and 250 μg/mL gentamycin, in accordance with an embodiment of the present invention.

FIG. 14 is a graphical illustration showing the effect of 2.43 pg/mL GM-CSF on 24-h PAO1 biofilm and synergy with 200 μg/mL tetracycline and 250 μg/mL gentamycin. A summary results table (Table 20) is provided below:

TABLE 20

Summary:

| % change in avg. CFU/ml of total viable cells | % change in avg. CFU/ml after adding factor + TET | % change in avg. CFU/ml after adding factor + GEN |
|---|---|---|
| −2.7% | −10.0% | −12.9% |

Example 7

Effects of GM-CSF on *P. aeruginosa* PDO300 Biofilm

After adding 2.43 pg/mL GM-CSF, the results show that the average CFU/ml of biofilm cells was reduced by 5.64% (average of 2 experiments). In comparison, the average CFU/ml of biofilm cells was reduced by 8.8%, 7.7%, 1.8% and 5.6% in the presence of 200 μg/mL ciprofloxacin, 200 μg/mL tobramycin, 200 μg/mL tetracycline and 200 μg/mL gentamicin, respectively.

Figure 15:
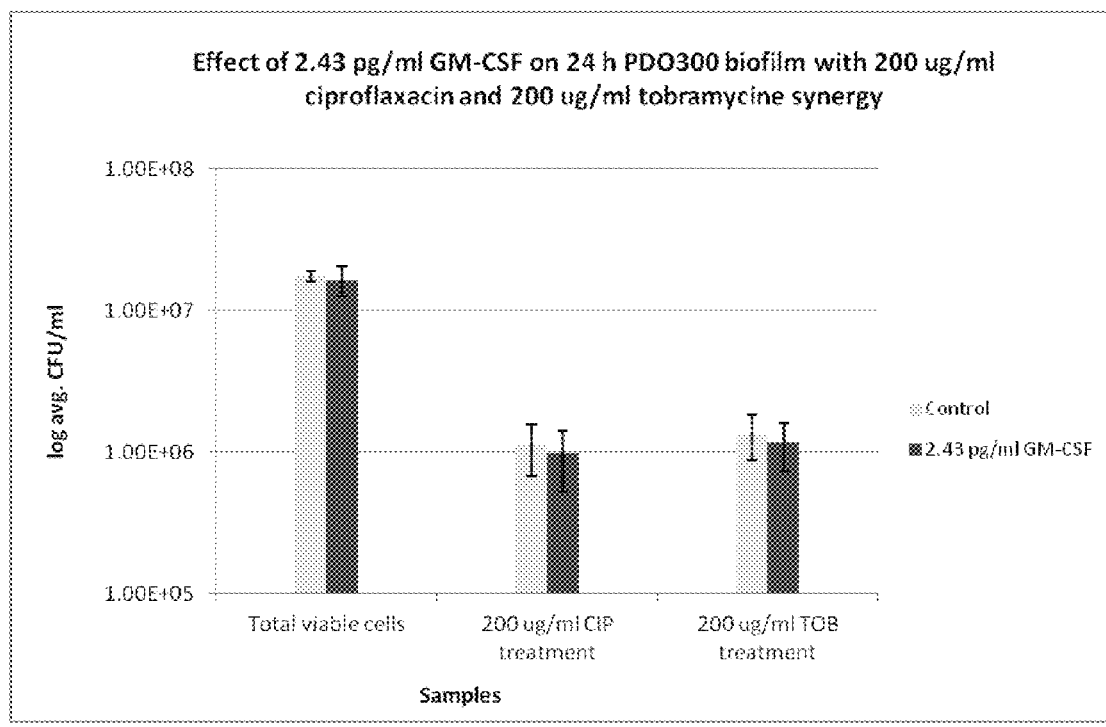
FIG. 15 is a graphical illustration showing the effect of 2.43 pg/mL GM-CSF on 24-h PDO300 biofilm and synergy with 200 μg/mL ciprofloxacin and 200 μg/mL tobramycin, in accordance with an embodiment of the present invention.

FIG. 15 is a graphical illustration showing the effect of 2.43 pg/mL GM-CSF on 24-h PDO300 biofilm and synergy with 200 μg/mL ciprofloxacin and 200 μg/mL tobramycin. A summary results table (Table 21) is provided below:

TABLE 21

Summary:

| % change in avg. CFU/ml of total viable cells | % change in avg. CFU/ml after adding factor + CIP | % change in avg. CFU/ml after adding factor + TOB |
|---|---|---|
| −5.7% | −14.0% | −13.0% |

Figure 16:
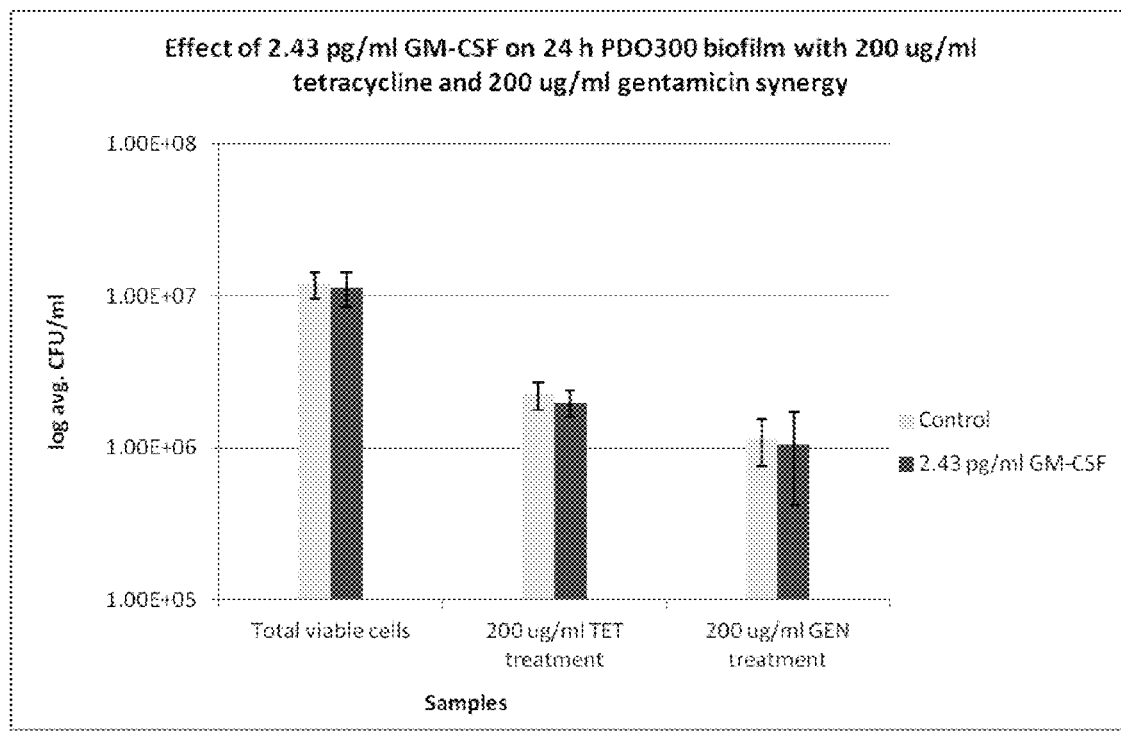
FIG. 16 is a graphical illustration showing the effect of 2.43 pg/ml GM-CSF on 24-h PDO300 biofilm and synergy with 200 μg/mL tetracycline and 200 μg/mL gentamicin, in accordance with an embodiment of the present invention.

FIG. 16 is a graphical illustration showing the effect of 2.43 pg/ml GM-CSF on 24-h PDO300 biofilm and synergy with 200 μg/mL tetracycline and 200 μg/mL gentamicin. A summary results table (Table 22) is provided below:

TABLE 22

Summary:

| % change in avg. CFU/ml of total viable cells | % change in avg. CFU/ml after adding factor + TET | % change in avg. CFU/ml after adding factor + GEN |
|---|---|---|
| −5.6% | −7.3% | −10.8% |

Example 4

Effects of GM-CSF on *E. coli* K12 Biofilm

After adding 2.43 pg/mL GM-CSF, the results show that the average CFU/mL of biofilm cells changed by +4.83% (average of 2 experiments). In the presence of an antibiotic, the average CFU/ml of biofilm cells was changed by +1.2%, +0.6%, −2.4% and +1.9% with 100 μg/mL ciprofloxacin, 100 μg/mL tobramycin, 100 μg/mL tetracycline and 125 μg/mL gentamicin, respectively.

The *E. coli* data suggest that GM-CSF has different effects on pathogens and the microbes in the host natural flora.

Figure 17:
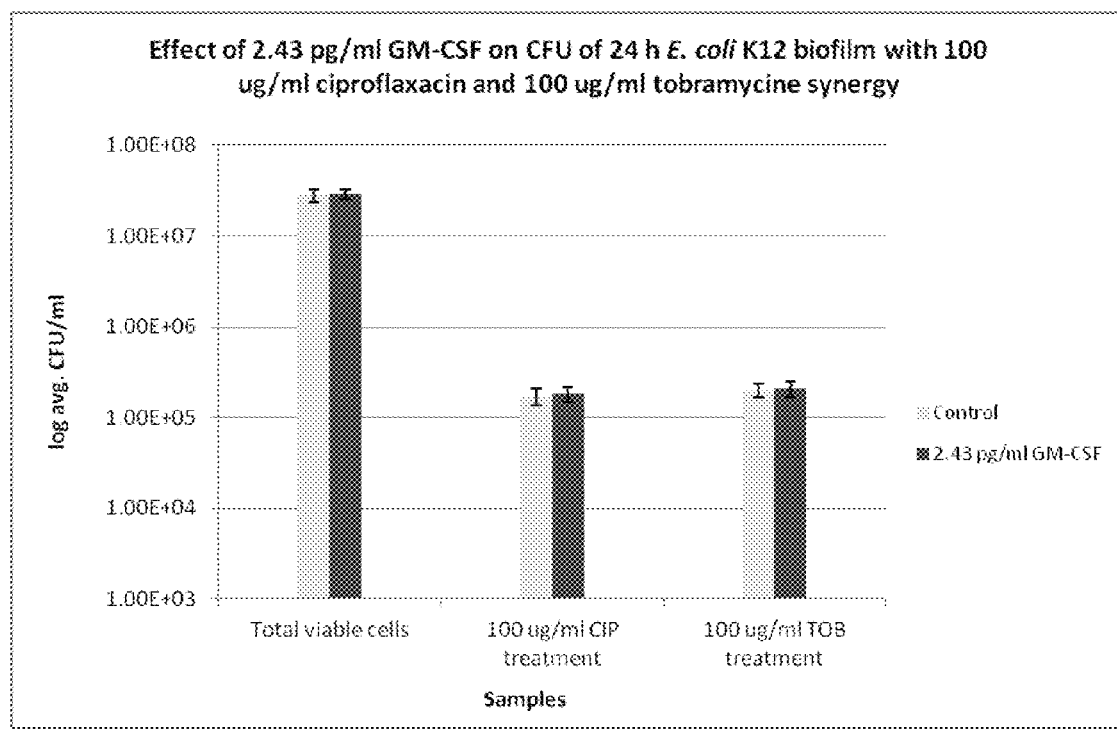
FIG. 17 is a graphical illustration showing the effect of 2.43 pg/mL GM-CSF on 24-h *E. coli* K12 biofilm and synergy with 100 μg/mL ciprofloxacin and 100 μg/mL tobramycin, in accordance with an embodiment of the present invention.

FIG. 17 is a graphical illustration showing the effect of 2.43 pg/mL GM-CSF on 24-h *E. coli* K12 biofilm and synergy with 100 μg/mL ciprofloxacin and 100 μg/mL tobramycin. A summary results table (Table 23) is provided below:

TABLE 23

Summary:

| % change in avg. CFU/ml of total viable cells | % change in avg. CFU/ml after adding factor + CIP | % change in avg. CFU/ml after adding factor + TOB |
|---|---|---|
| +3.6% | +4.8% | +4.2% |

Figure 18:
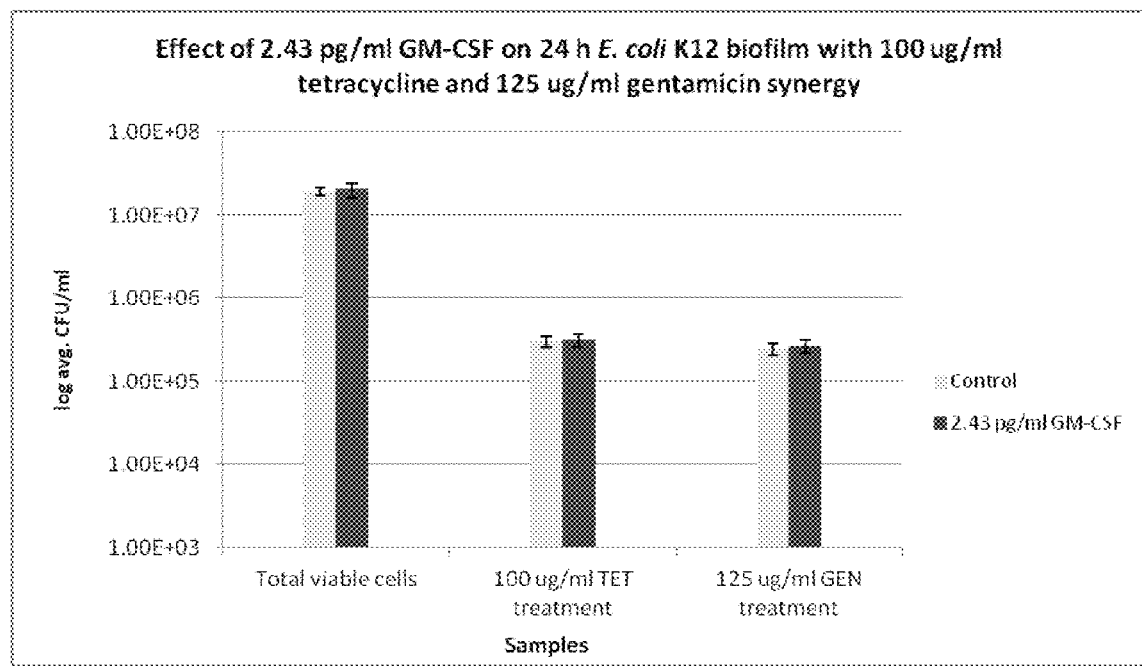
FIG. 18 is a graphical illustration showing the effect of 2.43 pg/mL GM-CSF on 24-h *E. coli* K12 biofilm and synergy with 100 μg/mL tetracycline and 125 μg/mL gentamicin, in accordance with an embodiment of the present invention.

FIG. 18 is a graphical illustration showing the effect of 2.43 pg/mL GM-CSF on 24-h *E. coli* K12 biofilm and synergy with 100 μg/mL tetracycline and 125 μg/mL gentamicin. A summary results table (Table 24) is provided below:

TABLE 24

Summary:

| % change in avg. CFU/ml of total viable cells | % change in avg. CFU/ml after adding factor + TET | % change in avg. CFU/ml after adding factor + GEN |
|---|---|---|
| +6.09% | +3.6% | +8.1% |

Example 5

Synergistic Effect of GM-CSF, Tobramycin and Alginate Lyase on Planktonic Cells of PDO300

This Example describes the use of alginate lyase as an enzyme to break down the extra alginate in order to understand the effect of the presence of alginate in PDO300 on the GM-CSF and antibiotic treatment.

To improve the effects of GM-CSF and antibiotics on the alginate overproducing PDO300, alginate lyase was used as an enzyme to break down the extra alginate. Alginate lyase is an enzyme which depolymerizes the alginate polymer by 13 elimination reaction. The alginate lyase used in the experiment was alginate lyase from *Flavobacterium* sp. (Sigma, catalog no. A1603-100MG). The experimental method was similar as mentioned above for the combined effect of GM-CSF and antibiotic. The alginate lyase was added as 0.05 mg/mL.

In brief, the experiment was performed in exponential phase with an optical density at 600 nm ($OD_{600}$) of 0.3 to 0.4. After preparing an overnight culture of the tested strain in 25 ml LB medium, a subculture was prepared with an $OD_{600}$ of 0.01 in 50 mL LB medium. The subculture was incubated at 37° C. with shaking at 200 rpm for 3-4 h, till $OD_{600}$ of 0.3 to 0.4 was reached. The exponential phase subculture was then divided equally into two centrifuge tubes. The subcultures were washed twice with 0.85% NaCl buffer by vortexing and then centrifuging at 4° C., 8000 rpm for 10 min each time. The washed subcultures were resuspended in 25 mL 0.85% NaCl buffer and vortexed gently for 1 min. One of the subculture was selected for isolation of persisters by adding 200 μg/mL ciprofloxacin. After adding the antibiotic, the subculture was incubated at 37° C. with shaking at 200 rpm for 3.5 h. The other subculture was used to quantify the total number of viable cells.

For testing the direct impact of GM-CSF on the total viable cells, 1 mL of the subculture was added in 24 microcentrifuge tubes; 12 were control and the other 12 were GM-CSF treatment samples. In the treatment samples, GM-CSF was added to a concentration of 2.43 pg/mL. The control samples were supplemented with the same concentration of PBS and BSA as present in 2.43 pg/mL GM-CSF samples. After incubation at 37° C. for 1 h with shaking at 200 rpm, the samples were plated on LB agar plates (with 15 g/L bacto agar) using drop plate method. The agar plates were then incubated for 24 h at 37° C. to count the total number of viable cells for studying the effect of 2.43 pg/mL GM-CSF on the viability of cells.

To test the synergy with antibiotic and alginate lyase, the samples were then incubated at 37° C. for 3.5 h with shaking at 200 rpm after adding the selected antibiotic alone and antibiotic with alginate lyase. After 3.5 h, the samples treated with antibiotic with and without alginate lyase were plated on LB agar plates and grown for 24 h at 37° C. to test the effect of killing with antibiotic and synergy with alginate lyase. After the persisters were isolated, the antibiotic was washed away with 0.85% NaCl buffer by centrifuging twice at 4° C. with shaking at 8000 rpm for 10 min and vortexed for 1 min after suspending in 0.85% NaCl buffer. The persisters were treated in a similar way as the total viable cells.

Example 6

Synergistic Effect of GM-CSF, Tobramycin and Alginate Lyase on Planktonic Cells of PDO300

Figure 19:
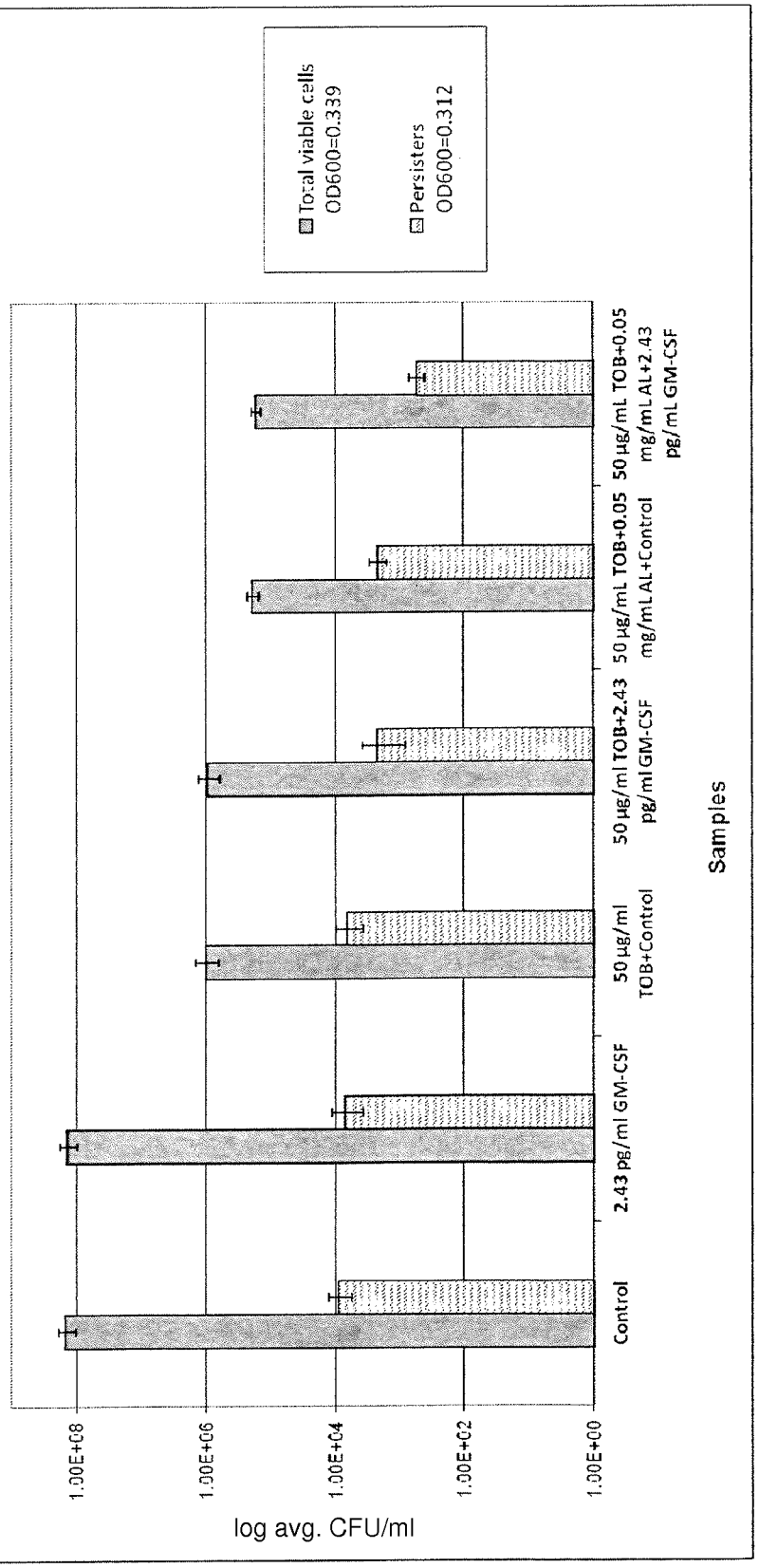
FIG. 19 is a graphical illustration showing the synergistic effects of 2.43 pg/mL GM-CSF, 50 μg/mL Tobramycin and 0.05 mg/mL alginate lyase on the planktonic normal and persister cells of PDO300, in accordance with an embodiment of the present invention.

This Example describes, for planktonic cells, the quantification of the viability of total cells and persister cells after treatment with (i) 2.43 pg/mL GM-CSF alone, (ii) 2.43 pg/mL GM-CSF and 50 μg/mL tobramycin and (iii) 2.43 pg/mL GM-CSF, 50 μg/mL tobramycin and 0.05 mg/mL Alginate lyase. After treatment of planktonic PAO1 cells with 2.43 pg/mL GM-CSF alone, the average CFU/mL of total viable cells changed by −6.3±2.1% and the persisters changed by −15.0±4.2%. When the cells were treated with 2.43 pg/mL GM-CSF and 50 μg/mL tobramycin, the total viable cells changed by −7.9±1.8% and the persisters changed by −63.6±5.4%. However, after the treatment with 2.43 pg/mL GM-CSF, 50 μg/mL tobramycin and 0.05 mg/mL Alginate lyase, the total viable cells changed by −11.02±3.0% and the persisters changed by −74.1±3.3%. FIG. 19 is a graphical illustration showing the synergistic effects of 2.43 pg/mL GM-CSF, 50 μg/mL Tobramycin and 0.05 mg/mL alginate lyase on the planktonic normal and persister cells of PDO300, in accordance with an embodiment of the present invention. With the addition of Alginate lyase, there was an enhanced killing of the persister cells which indicates that possibly the presence of alginate on PDO300 cells hinders the penetration of the factor. Addition of alginate lyase offered promising activity to control drug tolerance of PDO300 cells.

Example 7

Synergistic Effects of GM-CSF, Tobramycin and Alginate Lyase on Biofilm Cells of PDO300

This Example describes an experiment, similar to the one described in Example 5 with respect to the planktonic cells of PDO300, which was performed on the biofilm cells of PDO300.

In brief, after preparing an overnight culture, it was subcultured to an $OD_{600}$ of 0.01 in a total volume of 20 mL M63 medium with 316L stainless steel coupons (1.75 cm×1 cm). The biofilm was grown for 24 h at 37° C. After incubation, the coupons were washed by gently dipping in 0.85% NaCl buffer twice using tweezers and then placed in new empty petri dishes.

To test the synergistic effects of GM-CSF (2.43 pg/mL), tobramycin (200 μg/mL) and alginate lyase (0.5 mg/mL), a total of 8 coupons were included. These 8 coupons were placed in 8 microcentrifuge tubes with 2 mL of 0.85% NaCl buffer. There were 4 treatments samples, with 2 coupons for each treatment (i) Control (ii) 50 μg/mL Tobramycin (iii) 200 μg/mL Tobramycin and 2.43 pg/mL GM-CSF and (iv) 200 μg/mL Tobramycin, 2.43 pg/mL GM-CSF and 0.5 mg/mL Alginate lyase. The control samples were supplemented with the same amount of PBS and BSA as present in the samples with 2.43 pg/ml GM-CSF All the samples were incubated at 37 C, 3.5 h.

After incubation, each coupon was gently washed with 0.85% NaCl buffer and placed in a test tube with 2 mL of 0.85% NaCl buffer. They were sonicated (B200, Sinosonic Industrial Co., Ltd., Taiwan) for 1 min to release the biofilm cells from the biofilm. After vortexing for 1 min, the cell suspensions were plated on LB agar plates using drop plate method. The CFU was counted after incubation at 37° C. for 24 h to quantify the total number of viable cells. The synergistic effects of GM-CSF, tobramycin and alginate lyase were quantified based on CFU data.

Example 8

Synergistic Effect of GM-CSF, Tobramycin and Alginate Lyase on Biofilm Cells of PDO300

Figure 20:
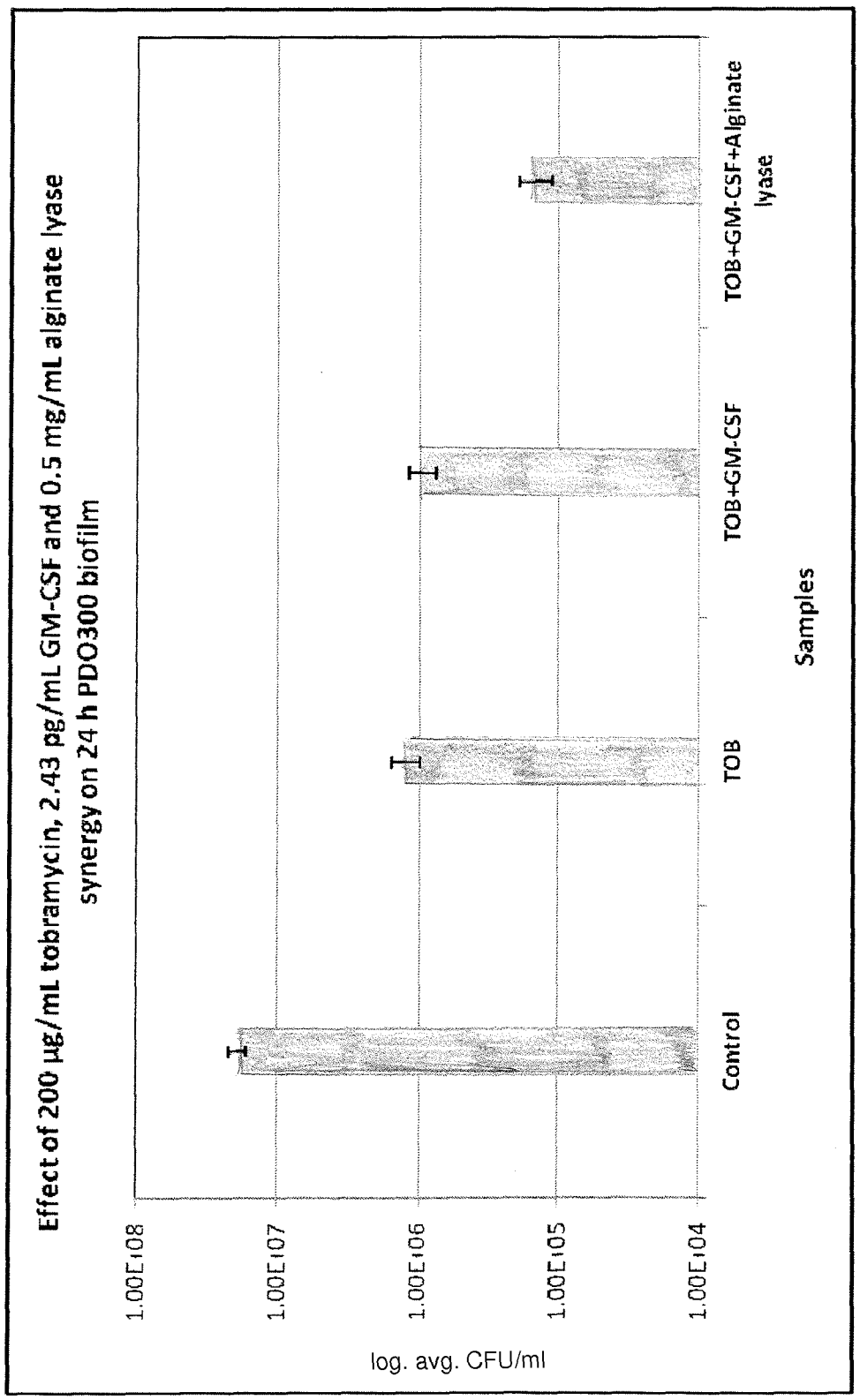
FIG. 20 is a graphical illustration showing the synergistic effect of 2.43 pg/mL GM-CSF, 200 μg/mL Tobramycin and 0.5 mg/mL alginate lyase on the biofilm cells of PDO300, in accordance with an embodiment of the present invention.

The results obtained from the experiment set forth in Example 7 show that after adding 2.43 pg/mL GM-CSF with 200 μg/mL tobramycin, there was an additional killing of biofilm cells by −24.7±5.3% compared to the 200 μg/mL tobramycin treatment alone. However, after adding 0.5 mg/mL alginate lyase, the change in the viable biofilm cells was −88.2±7.4%. FIG. 20 is a graphical illustration showing the synergistic effect of 2.43 pg/mL GM-CSF, 200 μg/mL Tobramycin and 0.5 mg/mL alginate lyase on the biofilm cells of PDO300, in accordance with an embodiment of the present invention. This indicates that the susceptibility of PDO300 to tobramycin was reduced because of the presence of excess alginate, which was eliminated by alginate lyase.

Example 9

GMCSF Binding Assays to Bacterial Whole Cell

This Example describes experiments conducted to determine the capability of GM-CSF to bind to whole cells of *P. aeruginosa* and *E. coli*. In brief, bacteria harvested at stationary phases of growth were washed with PBS and adjusted to $OD_{600}$ of 0.4 with PBS to ensure that an equal amount of cells was used for all GF-CSF binding tests. Suspensions of bacteria ($10^6$ CFU) were then incubated with and without different amount of recombinant human GM-CSF (rhGM-CSF, R&D systems) in a 40 µL volume at room temperature for 2 hours. After incubation, the cell suspension was centrifuged to separate supernatant (comprising buffer and unbound GM-CSF) and pellet (comprising cell and bound GM-CSF, if any), followed by the addition of 10 mM EDTA and boiling for 30 minutes to inactivate bacterial alkaline phosphatase activity. As control, PBS buffer with GM-CSF were processed in the similar manner. All the samples were then applied to Slot Blot (BioRad) for immunoblotting experiments. Anti-rhGMCSF developed in mice (Human GM-CSF MAb, Mouse IgG1, R&D system) was used as first antibody; Alkaline Phosphatase conjugated with Anti-mouse IgG was used to detect the binding of GM-CSF with BCIP/NBT (Promega) as substrates.

Cell Fractionation

Cell fractionation was done as described by George et al. (1986) with some modification. Briefly, cell pellets from stationary phase PAO1 were suspended in 1 ml of PBS buffer (pH7.2) containing 0.2 mg/mL lysozyme, protease inhibitor cocktail (Roche), chilled on ice, and sonicated (20 bursts, 10 s each at 70 W) with a Sonicator Q500 (Qsonica). The unbroken cells and debris were removed by centrifugation at 15,600×g for 5 min at 4° C. The supernatant was transferred to a 1.5 mL centrifuge tube, and the cell membranes were precipitated from the supernatant by centrifugation in a microcentrifuge at 15,600×g for 1 hour at 4° C. The supernatant was saved as cytoplasm fraction. To further separate inner and outer membrane proteins, the membrane pellets were thoroughly suspended in 0.1 ml of PBS buffer supplemented with 1% Sarkosyl by repeated pipetting. Following incubation for 30 minutes with intermittent mixing at room temperature, the suspension was centrifuged at 15,600×g for 1 hour at 4° C. The resulting pellet containing outermembrane proteins was suspended in 0.05 mL PBS and the supernatant was saved as solubilized inner membrane proteins.

Detection of GM-CSF Binding to Non-Denatured Membrane Proteins of *P. aeruginosa*

Different cellular components (30 µL) from *P. aeruginosa* were mixed with GM-CSF (20 ng) and incubated at room temperature for 2 hours. Samples were then suspended with sample loading buffer (125 mM Tris-HCl, pH 6.8, 50% glycerol), and separated by polyacrylamide gels in the Tris glycine system without SDS. The separated samples were then subjected to Western blotting and detected by Human GM-CSF Monoclonal Antibody as described in whole cell binding assay.

Figure 21:
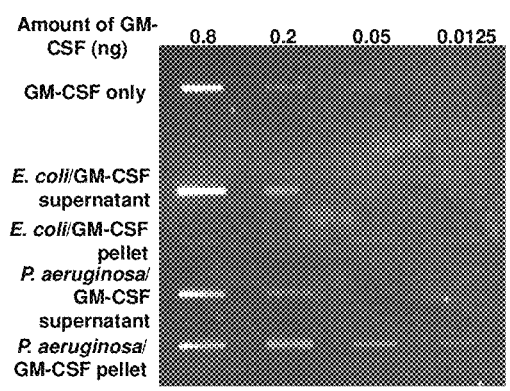
FIG. 21 shows that GM-CSF binds to *P. aeruginosa* cells, but not *E. coli* cells, according to an embodiment of the present invention.
Figure 22:
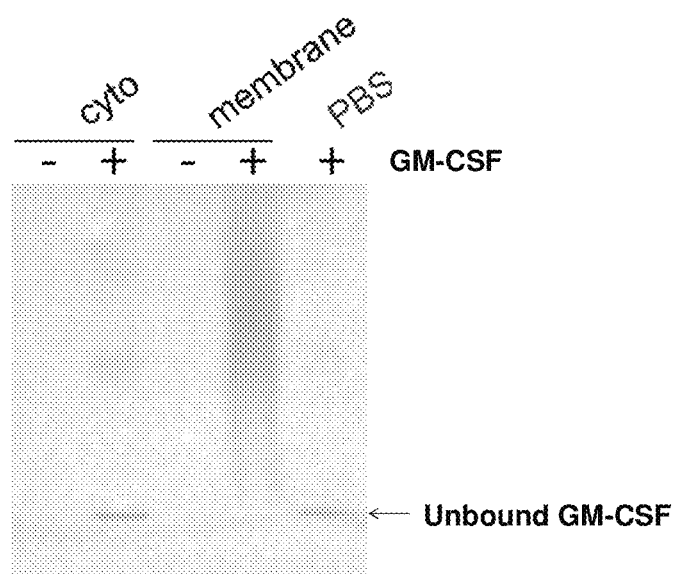
FIG. 22. is an immunoblot demonstrating that GM-CSF binds to membrane fractions of *P. aeruginosa*, according to an embodiment of the present invention.

The results show that *P. aeruginosa* has a receptor for GM-CSF. In particular, as shown in FIG. 21, GM-CSF does bind to whole cells of *P. aeruginosa*, but not *E. coli* (see the "pellet" samples in FIG. 21-Bacterial cells were collected, suspended in phosphate buffer saline (PBS) and mixed with or without different concentrations of GM-CSF at room temperature for 2 h. After incubation, the cell suspension was centrifuged to separate supernatant (comprising buffer and unbound GM-CSF) and pellet (comprising cell and bound GM-CSF, if any). Anti-rhGM-CSF from mice was used to detect GM-CSF using Western blotting). Furthermore, by incubating GM-CSF with different cellular components followed by Western blotting under non-denatured condition, it was found that GM-CSF preferentially binds to membrane fractions of *P. aeruginosa* (see FIG. 22-Immunoblot demonstrates that GM-CSF binds to membrane fractions of *P. aeruginosa*. Fractionated proteins incubated GM-CSF were separated by nondenatured-PAGE and detected by Western blotting using anti-rhGM-CSF as the first antibody). Such binding was found to be sensitive to protease treatment (data not shown). Collectively, these results indicate that GM-CSF can bind to a specific protein receptor on *P. aeruginosa* cell surface and modulate bacterial persistence.

Overall, the data from these experiments suggest that some host immune factors, such as GM-CSF, have unreported potent effects on persister cells of bacterial pathogens, but may not have such effects on the non-pathogenic microbes in the natural flora of the host (as shown with *E. coli* here). These factors can potentiate the antibiotics to eliminate persister cells, a promising activity for treating chronic infections. For example, GM-CSF at 2.43 pg/mL level was found to render more than 97% of persister cells of the human pathogen *P. aeruginosa* sensitive to the antibiotic ciprofloxacin. In addition to ciprofloxacin, GM-CSF was also found to potentiate multiple classes of antibiotics and exhibited activities against *P. aeruginosa* persister cells both in planktonic cultures and in surface-attached biofilms. Although the effects on biofilms were not as potent as those against planktonic persister cells, stronger effects were observed when the biofilms were co-treated with alginate lyase.

While several embodiments of the invention have been discussed, it will be appreciated by those skilled in the art that various modifications and variations of the present invention are possible. Such modifications do not depart from the spirit and scope of the present invention.

What is claimed is:

1. A method for reducing the number of viable bacterial persister cells in a population of persister cells, comprising the steps of:
    providing a population of cells comprising a sub-population of normal cells and a sub-population of persister *Pseudomonas aeruginosa* cells;
    isolating the sub-population of persister cells from the sub-population of normal cells, by contacting the population with an antibiotic, wherein the antibiotic is ciprofloxacin;
    contacting at least one persister cell in the sub-population of persister cells, with a human immune factor, wherein said human immune factor is GM-CSF, and with a predetermined amount of at least one antibiotic wherein said at least one antibiotic is selected from the group consisting of tobramycin, ciprofloxacin, and tetracycline, wherein the step of contacting results in reduction of viable persister cells in the sub-population of persister cells.

2. The method of claim 1, wherein the GM-CSF is made by one or multiple domains of GM-CSF.

3. The method of claim 1, further comprising the step of contacting at least one persister cell in the population of persister cells with a predetermined amount of alginate lyase.

* * * * *